United States Patent
Nash et al.

(10) Patent No.: US 10,293,164 B2
(45) Date of Patent: May 21, 2019

(54) APPARATUS AND METHODS FOR ASSISTED BREATHING BY TRANSVASCULAR NERVE STIMULATION

(71) Applicant: Lungpacer Medical Inc., Burnaby (CA)

(72) Inventors: John E. Nash, Chester Spring, PA (US); Douglas G. Evans, Downingtown, PA (US); Viral Thakkar, Burnaby (CA)

(73) Assignee: Lungpacer Medical Inc., Burnaby (CA)

( * ) Notice: Subject to any disclaimer, the term of this patent is extended or adjusted under 35 U.S.C. 154(b) by 0 days.

(21) Appl. No.: 15/606,867

(22) Filed: May 26, 2017

(65) Prior Publication Data
US 2018/0339156 A1     Nov. 29, 2018

(51) Int. Cl.
*A61N 1/36*     (2006.01)
*A61N 1/05*     (2006.01)

(52) U.S. Cl.
CPC .......... *A61N 1/3611* (2013.01); *A61N 1/0551* (2013.01); *A61N 1/36185* (2013.01)

(58) Field of Classification Search
None
See application file for complete search history.

(56) References Cited

U.S. PATENT DOCUMENTS

| | | |
|---|---|---|
| 1,693,734 A | 12/1928 | Waggoner |
| 2,532,788 A | 12/1950 | Sarnoff |
| 2,664,880 A | 1/1954 | Wales, Jr. |
| 3,348,548 A | 10/1967 | Chardack |
| 3,470,876 A | 10/1969 | John |

(Continued)

FOREIGN PATENT DOCUMENTS

| | | |
|---|---|---|
| CN | 1652839 A | 8/2005 |
| CN | 102143781 A | 8/2011 |

(Continued)

OTHER PUBLICATIONS

Atonica A., et al., "Vagal Control of Lymphocyte Release from Rat Thymus," Journal of the Autonomic Nervous System, Elsevier, vol. 48(3), Aug. 1994, pp. 187-197.

(Continued)

*Primary Examiner* — Carl H Layno
*Assistant Examiner* — Jennifer L Ghand
(74) *Attorney, Agent, or Firm* — Bookoff McAndrews, PLLC

(57) ABSTRACT

A catheter may include an outer layer defining a plurality of apertures therethrough, and a body defining at least one longitudinal lumen therein. The body may be within the outer layer, and the apertures may be radially outward of the lumen. The catheter may also include a plurality of electrodes positioned in or on the catheter, with each electrode being electrically exposed through an aperture of the plurality of apertures. A ribbon cable may extend through the lumen and include a plurality of leads, with the plurality of leads being electrically connected to the plurality of electrodes. The plurality of leads and electrodes may be formed by the deposition of conductive inks or paints, or by the electrodeposition of copper or other conductive metals or materials.

22 Claims, 12 Drawing Sheets

(56) References Cited

U.S. PATENT DOCUMENTS

| | | |
|---|---|---|
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | McCormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,249,708 B1 * | 6/2001 | Nelson .................. A61N 1/056 607/122 |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |

(56) References Cited

U.S. PATENT DOCUMENTS

| | | |
|---|---|---|
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,082,331 B1 | 7/2006 | Park et al. |
| 7,130,700 B2 * | 10/2006 | Gardeski ............ A61M 25/0021 607/122 |
| 7,142,903 B2 | 11/2006 | Rodriguez et al. |
| 7,149,585 B2 | 12/2006 | Wessman et al. |
| 7,155,278 B2 | 12/2006 | King et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van Venrooij et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |

(56) References Cited

U.S. PATENT DOCUMENTS

| | | |
|---|---|---|
| 8,626,292 B2 | 1/2014 | McCabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,149,642 B2 | 10/2015 | McCabe et al. |
| 9,168,377 B2 | 10/2015 | Hoffer |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,474,894 B2 | 10/2016 | Mercanzini et al. |
| 9,485,873 B2 | 11/2016 | Shah et al. |
| 9,498,625 B2 | 11/2016 | Bauer et al. |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,396 B2 | 5/2018 | Young et al. |
| 9,968,785 B2 | 5/2018 | Hoffer et al. |
| 9,968,786 B2 | 5/2018 | Bauer et al. |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |

(56) References Cited

U.S. PATENT DOCUMENTS

| | | |
|---|---|---|
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1* | 9/2006 | Spinka ............... A61B 5/0422 607/116 |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1* | 2/2007 | Paul ............... A61B 18/1492 606/41 |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0248122 A1* | 10/2009 | Pianca ............... A61N 1/0551 607/115 |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2010/0022950 A1 | 1/2010 | Anderson et al. |
| 2010/0036451 A1* | 2/2010 | Hoffer ............... A61N 1/0558 607/42 |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0085580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0148877 A1* | 5/2015 | Thakkar ............... A61N 1/05 607/116 |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0231348 A1 | 8/2015 | Lee et al. |
| 2015/0250982 A1 | 9/2015 | Osypka |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De La Rama et al. |
| 2015/0374991 A1 | 12/2015 | Morris et al. |
| 2016/0001072 A1 | 1/2016 | Gelfand et al. |
| 2016/0101280 A1* | 4/2016 | Thakkar ............... A61N 1/05 607/116 |

(56) References Cited

U.S. PATENT DOCUMENTS

| | | |
|---|---|---|
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 2489395 A1 | 8/2012 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | 9407564 A2 | 4/1994 |
| WO | 9508357 A1 | 3/1995 |
| WO | 9964105 A1 | 12/1999 |
| WO | 9965561 A1 | 12/1999 |
| WO | 0100273 A1 | 1/2001 |
| WO | 02058785 A1 | 8/2002 |
| WO | 03094855 A1 | 11/2003 |
| WO | 2006110338 A1 | 10/2006 |
| WO | 2006115877 A1 | 11/2006 |
| WO | 2007053508 A1 | 5/2007 |
| WO | 2008092246 A1 | 8/2008 |
| WO | 2008094344 A1 | 8/2008 |
| WO | 2009006337 A1 | 1/2009 |
| WO | 2009134459 A2 | 11/2009 |
| WO | 2010029842 A1 | 3/2010 |
| WO | 2010148412 A1 | 12/2010 |
| WO | 2011158410 A1 | 12/2011 |
| WO | 2012106533 A2 | 8/2012 |
| WO | 2013131187 A1 | 9/2013 |
| WO | 2013188965 A1 | 12/2013 |
| WO | 2015075548 A1 | 5/2015 |
| WO | 2015109401 A1 | 7/2015 |

OTHER PUBLICATIONS

Whaley K., et al., "C2 Synthesis by Human Monocytes is Modulated by a Nicotinic Cholinergic Receptor," Nature, vol. 293, Oct. 15, 1981, pp. 580-582 (and reference page).

Borovikovaa L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.

Borovikovaa L.V., et al., "Vagus Nerve Stimulation Attenuates the Systemic Inflammatory Response to Endotoxin," Mature, Macmillan Magazines Ltd, vol. 405, May 25, 2000, pp. 458-462.

Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

Extended European Search Report for Application No. 14864542.7, dated Jun. 2, 2017, 8 pages.

Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.

Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.

Gupta A.K., "Respiration Rate Measurement Based on Impedance Pneumography," Data Acquisition Products, Texas Instruments, Application Report, SBAA181, Feb. 2011, 11 pages.

Guslandi M., "Nicotine Treatment for Ulcerative Colitis," The British Journal of Clinical Pharmacology, Blackwell Science Ltd, vol. 48, 1999, pp. 481-484.

Japanese Office Action in corresponding Japanese Application No. 2014-560202, dated Dec. 6, 2016, 4 pages.

Kawashima K., et al., "Extraneuronal Cholinergic System in Lymphocytes," Pharmacology & Therapeutics, Elsevier, vol. 86, 2000, pp. 29-48.

Madretsma, G.S., et al., "Nicotine Inhibits the In-vitro Production of Interleukin 2 and Tumour Necrosis Factor-α by Human Mononuclear Cells," Immunopharmacology, Elsevier, vol. 35 (1), Oct. 1996, pp. 47-51.

Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.

Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.

Planas R.F., et al., "Diaphragmatic Pressures: Transvenous vs. Direct Phrenic Nerve Stimulation," Journal of Applied Physiology, vol. 59(1), 1985, pp. 269-273.

Romanovsky, A.A., et al., "The Vagus Nerve in the Thermoregulatory Response to Systemic Inflammation," American Journal of Physiology, vol. 273 (1 Pt 2), 1997, pp. R407-R413.

Salmela L., et al., "Verification of the Position of a Central Venous Catheter by Intra-Atrial ECG. When does this method fail?," Acta Anasthesiol Scand, Vol. 37 (1), 1993, pp. 26-28.

Sandborn W.J., "Transdermal Nicotine for Mildly to Moderately Active Ulcerative Colitis," Annals of Internal Medicine, vol. 126 (5), Mar. 1, 1997, pp. 364-371.

Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.

Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.

Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.

Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.

(56) References Cited

OTHER PUBLICATIONS

Scheinman R.I., et al., "Role of Transcriptional Activation of IκBα in Mediation of Immunosuppression by Glucocorticoids," Science, vol. 270, Oct. 13, 1995, pp. 283-286.
Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.
Steinlein, O., "New Functions for Nicotinic Acetylcholine Receptors?," Behavioural Brain Research, vol. 95, 1998, pp. 31-35.
Sternberg E.M., (Series Editor) "Neural-Immune Interactions in Health and Disease," The Journal of Clinical Investigation, vol. 100 (11), Dec. 1997, pp. 2641-2647.
Sykes., A.P., et al. "An Investigation into the Effect and Mechanisms of Action of Nicotine in Inflammatory Bowel Disease," Inflammation Research, vol. 49, 2000, pp. 311-319.
Toyabe S., et al., "Identification of Nicotinic Acetylcholine Receptors on Lymphocytes in the Periphery as well as Thymus in Mice," Immunology, vol. 92, 1997, pp. 201-205.
Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.
Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.
Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.
Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.
Chinese Search Report for Application No. CN2013/80023357.5, dated Jul. 24, 2015.
Co-pending U.S. Appl. No. 15/606,867, filed May 26, 2017.
Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.
Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.
De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.
Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.
European Search Report for Application No. 13758363, dated Nov. 12, 2015.
European Search Report for Application No. EP17169051.4, dated Sep. 8, 2017, 7 pages.
Extended European Search Report for Application No. 15740415.3, dated Jul. 7, 2017.
Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Japanese Office Action in corresponding Japanese Application No. 2014-560202, dated Oct. 17, 2017, 5 pages.
Levine S., et al., "Rapid disuse atrophy of diaphragm fibers in mechanically ventilated humans," New England Journal of Medicine, 2008, vol. 358, pp. 1327-1335.
Lungpacer: Therapy, News . . . Accessed Dec. 27, 2016.
Marcy, T.W. et al., "Diaphragm Pacing for Ventilatory Insufficiency," Journal of Intensive Care Medicine, 1987, vol. 2 (6), pp. 345-353.
Meyyappan R., "Diaphragm Pacing during Controlled Mechanical Ventilation: Pre-Clinical Observations Reveal a Substantial Improvement in Respiratory Mechanics", 17th Biennial Canadian Biomechanics Society Meeting, Burnaby, BC, Jun. 6-9, 2012.
Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-to-Wean Intensive Care Unit Patients," Surgical Endoscopy, 2007, vol. 21, pp. 475-479.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Wanner, A. et al., "Trasvenous Phrenic Nerve Stimulation in Anesthetized Dogs," Journal of Applied Physiology, 1973, vol. 34 (4), pp. 489-494.
PCT Search Report dated Oct. 26, 2018 for PCT Application No. PCT/IB2018/000603, 7 pages.

\* cited by examiner

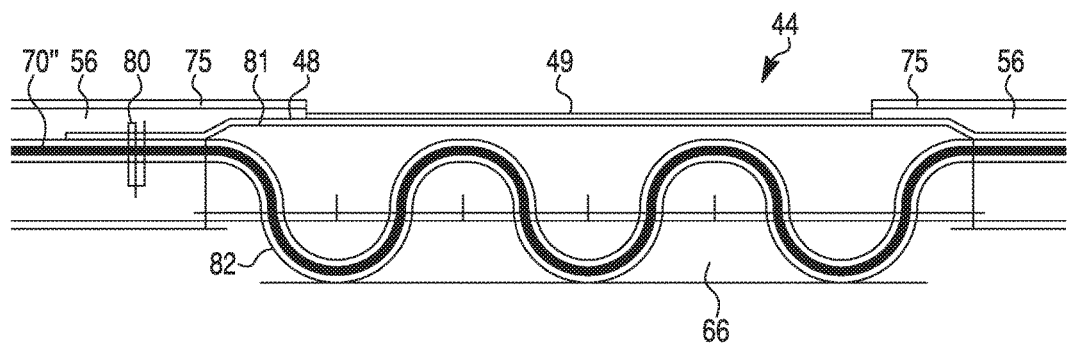
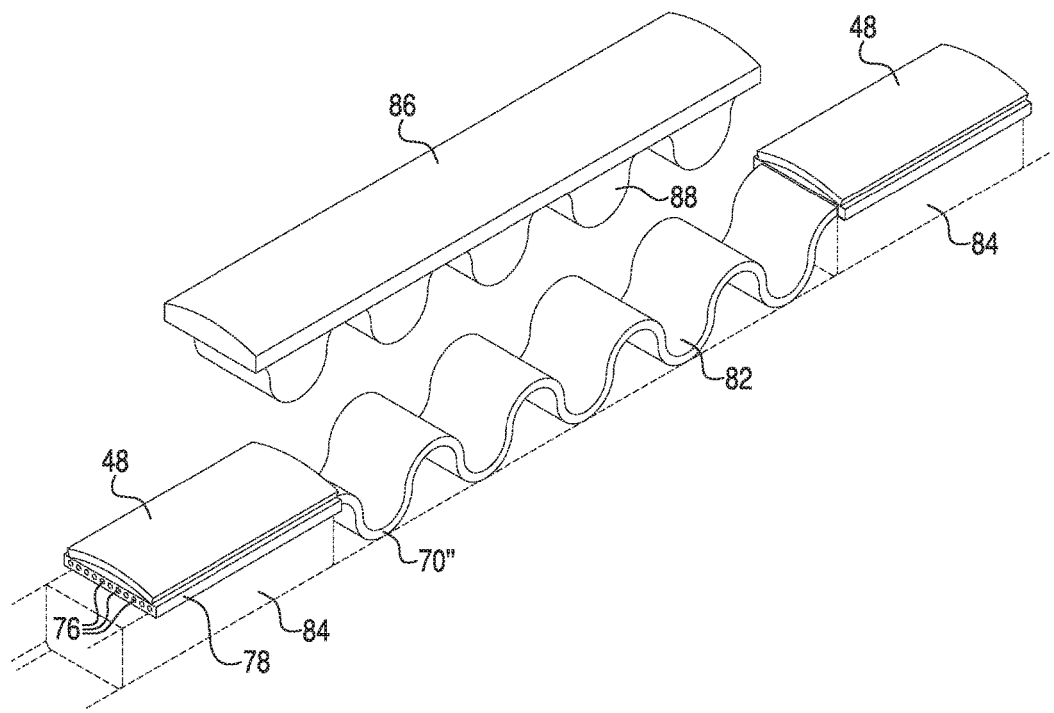

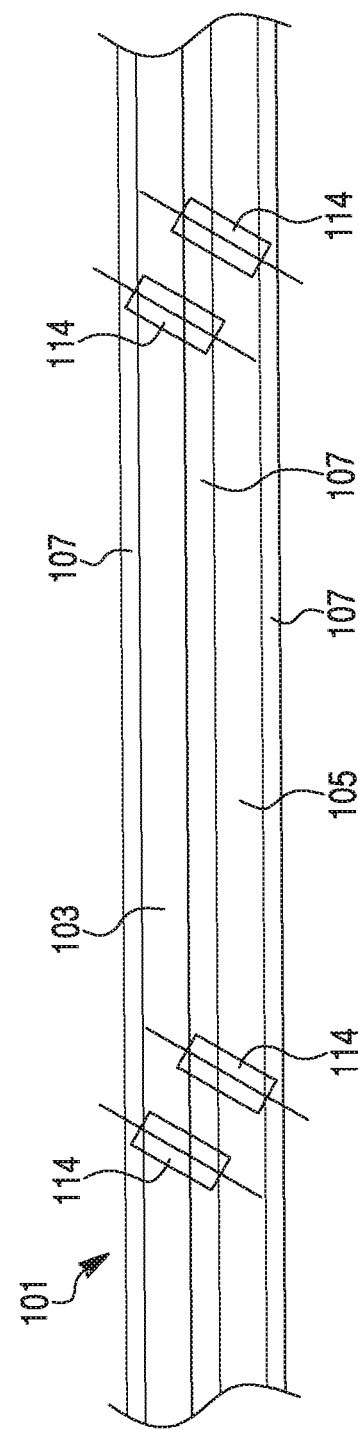

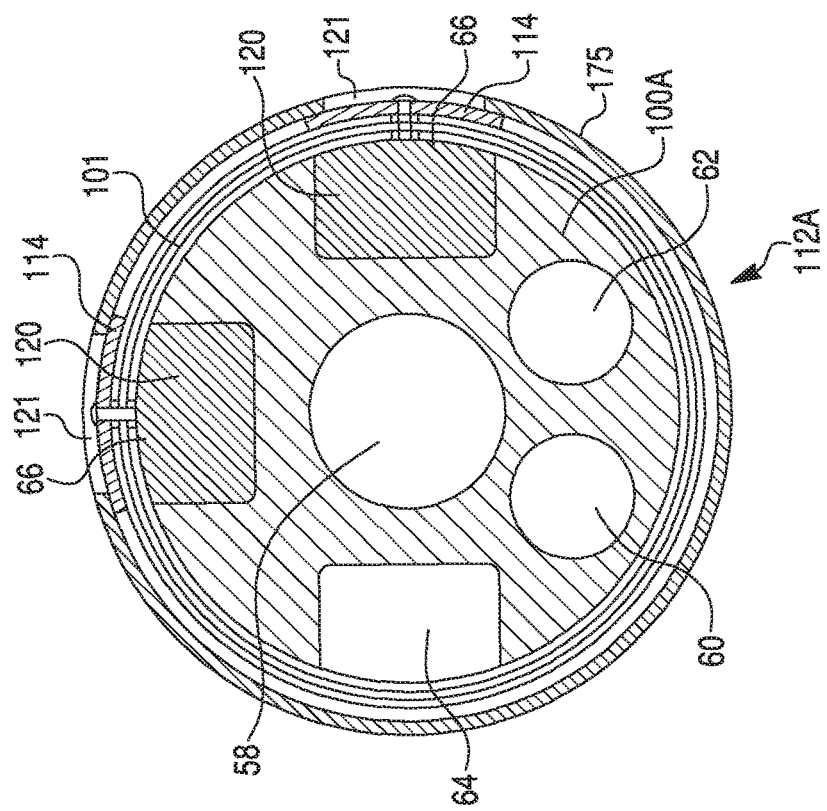
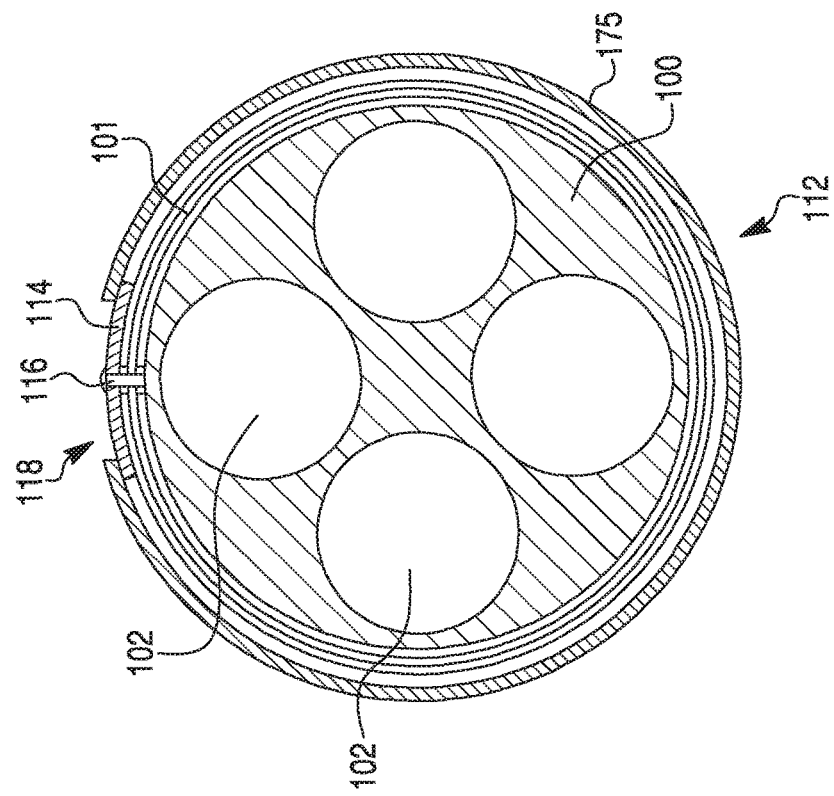

APPARATUS AND METHODS FOR ASSISTED BREATHING BY TRANSVASCULAR NERVE STIMULATION

TECHNICAL FIELD

Embodiments of this disclosure relate to medical apparatus and particularly to apparatus applicable for the restoration, enhancement, or modulation of physiological functions. Specific embodiments provide apparatus for stimulating the phrenic nerves to contract the diaphragm muscle to assist breathing by transvascular electrical stimulation of nerves.

BACKGROUND

Electrical stimulation of nerves is widely applied in the treatment of a range of conditions and may be applied to control muscle activity or to generate sensations. Muscles and nerves may be stimulated by placing electrodes in, around, or near the muscles and nerves and by activating the electrodes by means of an implanted or external source of energy (e.g. electricity).

The diaphragm muscle provides important functions for respiration. The phrenic nerves normally transmit signals from the brain to cause the contractions of the diaphragm muscle necessary for breathing. However, various conditions can prevent appropriate signals from being delivered to the phrenic nerves. These include:
  permanent or temporary injury or disease affecting the spinal cord or brain stem;
  Amyotrophic Lateral Sclerosis (ALS);
  decreased day or night ventilatory drive (e.g. central sleep apnea, Ondine's curse); and
  decreased ventilatory drive while under the influence of anesthetic agents and/or mechanical ventilation.
These conditions affect a significant number of people.

Intubation and positive pressure mechanical ventilation (MV) may be used for periods of several hours or several days, sometimes weeks, to help critically ill patients breathe while in intensive care units (ICU). Some patients may be unable to regain voluntary breathing and thus require prolonged or permanent mechanical ventilation. Although mechanical ventilation can be initially lifesaving, it has a range of significant problems and/or side effects. Mechanical ventilation:
  often causes ventilator-induced lung injury (VILI) and alveolar damage which can lead to accumulation of fluid in the lungs and increased susceptibility to infection (ventilator-associated pneumonia; VAP);
  commonly requires sedation to reduce discomfort and anxiety in acutely intubated patients;
  leads to rapid atrophy of the disused diaphragm muscle (ventilator-induced diaphragm dysfunction, VIDD);
  can adversely affect venous return because the lungs are pressurized and the diaphragm is inactive;
  interferes with eating and speaking;
  requires apparatus that is not readily portable; and
  increases the risk of dying if the patient fails to regain normal breathing and becomes ventilator-dependent.

A patient who is sedated and connected to a mechanical ventilator cannot breathe normally because the central neural drive to the diaphragm and accessory respiratory muscles is suppressed. Inactivity leads to muscle disuse atrophy and an overall decline in well-being. Diaphragm muscle atrophy occurs rapidly and can be a serious problem to the patient. According to a published study in organ donor patients (Levine et al., New England Journal of Medicine, 358: 1327-1335, 2008) after only 18 to 69 hours of mechanical ventilation, all diaphragm muscle fibers had shrunk on average by 52-57%. Muscle fiber atrophy results in muscle weakness and increased fatigability. Therefore, ventilator-induced diaphragm atrophy could cause a patient to become ventilator-dependent. It has been estimated that over 600,000 US patients will be ventilator dependent and require prolonged mechanical ventilation by the year 2020 (Zilberberg et al., Critical Care Medicine, 36(5): 1451-1455, 2008).

It may also be necessary during MV to deliver or remove one or more fluids or to obtain sensor readings from within the patient. Smaller patients, such as, for example, neonates, may require smaller medical instruments to perform the aforementioned procedures. Additionally, as with any medical procedure, the risk of injury to the patient increases with the length and complexity of the medical procedure.

There remains a need for cost-effective, practical, surgically simple and minimally invasive apparatus and methods that may be applied to stimulate breathing, deliver treatment, and perform tests. There is also a need for apparatus and methods for facilitating patients on MV to regain the capacity to breathe naturally and to be weaned from MV.

SUMMARY

Embodiments of the present disclosure relate to, among other things, medical apparatus and methods for nerve stimulation. Specific embodiments provide apparatus for stimulating breathing by trans-vascular electrical stimulation of nerves. Each of the embodiments disclosed herein may include one or more of the features described in connection with any of the other disclosed embodiments.

In one embodiment, a catheter may include an outer layer defining a plurality of apertures therethrough, and a body defining at least one longitudinal lumen therein. The body may be within the outer layer, and the apertures may be radially outward of the lumen. A plurality of electrodes may be positioned in or on the catheter, and each electrode may be electrically exposed through an aperture of the plurality of apertures, or alternatively mounted on the surface of the catheter. A ribbon cable may extend through the lumen and include a plurality of leads. The plurality of leads may electrically connect to the plurality of electrodes.

The catheter may further include one or more of the following features. The lumen may be a groove or recessed channel exposed along a portion of the circumference of the body along at least a portion of the length of the body, and the groove may be at least partially covered by an outer layer. The plurality of leads may be at least partially surrounded by a non-conducting material. The ribbon cable may include a plurality of corrugations. The catheter may also include at least one filler positioned within at least a portion of the corrugations. The corrugations may be positioned radially inward of at least one electrode. The catheter may also include at least one fluid lumen and a guide wire lumen.

Further, the catheter may include a connector feed and an application specific integrated circuit ("ASIC") radially inward of the outer layer. The ASIC may connect the connector feed to the ribbon cable. The ribbon cable may include several, for example three, branches of ribbon cable, and the at least one longitudinal lumen may include three longitudinal lumens spaced circumferentially around an exterior of the body and radially inward of the outer layer. In this example, the three branches may extend distally from the ASIC, and each of the three branches may connect to at least one electrode through a corresponding longitudinal lumen. One branch of the three branches may include at least one lead that electrically connects at least one proximal electrode and at least one other lead that electrically connects at least one distal electrode. The plurality of apertures may include a plurality of proximal apertures and a plurality of distal apertures. The proximal apertures may include two longitudinally extending rows, and the distal apertures may include two longitudinally extending rows. One row of proximal apertures may be circumferentially aligned with one row of distal apertures. The ribbon cable may be electrically connected to at least one electrode via a connection and an electrode coupler, and the electrode coupler may longitudinally overlap with the ribbon cable and be positioned radially inward of a portion of the electrode.

In another alternative or additional embodiment, the catheter may include an outer layer defining a plurality of apertures therethrough, and a body radially within the outer layer. The catheter may also include a radial extension, extending helically around and radially outward from the body and within the outer layer, as well as a ribbon cable coupled to a plurality of electrodes. The ribbon cable may extend around an exterior of the body between portions of the radial extension, with each electrode of the plurality of electrodes electrically exposed through an aperture of the plurality of apertures, the apertures in this case being formed in an outer insulating layer over the electrodes.

The catheter may further include one or more of the following features. The plurality of electrodes may be coupled to the ribbon cable at approximately a 45 degree angle relative to a longitudinal axis of the ribbon cable. The catheter may include at least one ASIC positioned radially inward of the outer layer, and the at least one ASIC may electrically connect the ribbon cable to at least one of the plurality of electrodes. The body may include at least one groove exposed along a circumference of the body along at least a portion of the length of the body, and the at least one ASIC may be positioned within the at least one groove. The catheter may include at least one ASIC for each of the plurality of electrodes, and each ASIC may electrically connect the ribbon cable to the corresponding electrode. The catheter may include a conductive liner positioned over or within the apertures.

In another alternative or additional embodiment, the catheter may include an outer layer or sleeve. The outer layer may include first and second longitudinally extending rows of distal apertures in the outer layer, and the outer layer and/or the catheter may also include a first radiopaque feature for confirming an orientation of the first row of distal apertures relative to the second row of distal apertures.

The catheter may further include one or more of the following features. The catheter may further include first and second longitudinally extending rows of proximal apertures in the outer layer. The outer layer may include a second radiopaque feature for confirming an orientation of the first row of proximal apertures relative to the second row of proximal apertures. The first row of proximal apertures may be circumferentially aligned with one of either the first row of distal apertures or the second row of distal apertures. The second row of proximal apertures may be circumferentially offset from both the first row of distal apertures and the second row of distal apertures. The second radiopaque feature may include a radiopaque marker positioned circumferentially opposite to a line extending between the first and second rows of proximal apertures. The first radiopaque feature may be at a distal portion of the outer layer, and the second radiopaque feature may be at a proximal portion of the outer layer. The catheter may further include a hub, and the hub may include an orientation feature. The hub may also include a port configured to couple the hub to a proximal portion of the catheter in a particular orientation.

Further aspects of the disclosures and features of example embodiments are illustrated in the appended drawings and/or described in the text of this specification and/or described in the accompanying claims. It may be understood that both the foregoing general description and the following detailed description are exemplary and explanatory only and are not restrictive of the invention, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate non-limiting embodiments of the present disclosure and together with the description serve to explain the principles of the disclosure.

FIG. 7A illustrates an exemplary embodiment of a conductor and electrode assembly of a catheter, and FIG. 7B illustrates an exploded view of another exemplary embodiment of a conductor and electrode assembly.

FIG. 9 illustrates a portion of a conductive ribbon cable with electrodes that may be coupled around the tubular member of FIG. 8 within the radial extension, according to an exemplary embodiment.

FIG. 10 illustrates a cross-sectional view of a catheter with the exemplary tubular member of FIG. 8 and the ribbon cable with electrodes of FIG. 9, according to an exemplary embodiment.

FIG. 11 illustrates a cross-sectional view of a catheter with an exemplary tubular member similar to FIG. 6 with a plurality of application specific integrated circuits.

DETAILED DESCRIPTION

Figure 1:
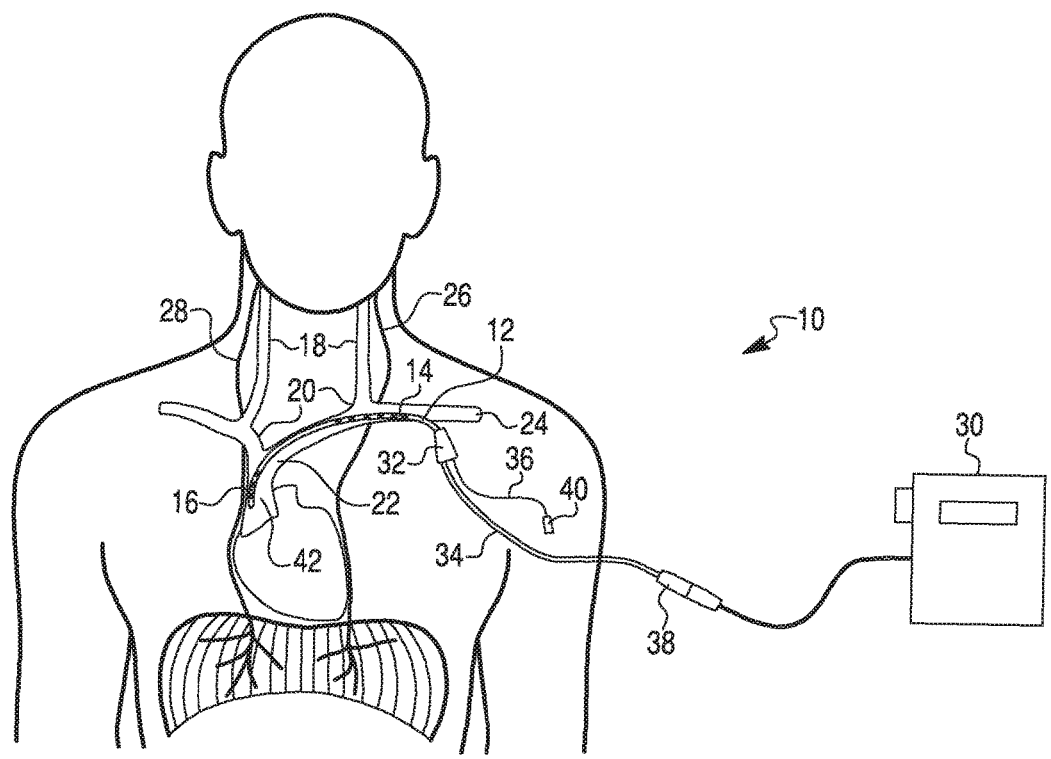
FIG. 1 illustrates the anatomy of selected nerves and blood vessels in a person's neck and upper torso, along with an exemplary catheter and control unit.

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative, rather than a restrictive, sense.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

General Overview

In general, embodiments of this disclosure relate to medical devices and methods for electrically stimulating a patient's nerves. In one embodiment, the patient's nerves may be stimulated to activate the diaphragm to restore or control breathing.

The medical devices described herein may include several components, including a catheter having a tubular member and one or more electrode assemblies, a signal generator to provide stimulation energy to the electrode assemblies, and one or more sensors to sense the condition of the patient and adjust the stimulation signals. The medical devices may further include a steering mechanism. Various embodiments of catheters are disclosed, including windowed catheters, multi-lumen catheters, and radiopaque catheters. In addition, various embodiments of electrode assemblies are disclosed, which may be used alone, in combination with other electrode assemblies, and with any of the disclosed tubular members that form the outer portion of the catheters.

The different embodiments of the various medical device components (e.g., electrode assemblies, steering mechanisms, etc.) may be combined and used together in any logical arrangement. Furthermore, individual features or elements of any described embodiment may be combined with or used in connection with the individual features or elements of other embodiments. The various embodiments may further be used in different contexts than those specifically described herein. For example, the disclosed electrode structures may be combined or used in combination with various deployment systems known in the art for various diagnostic and/or therapeutic applications.

During use, the medical devices (e.g., a catheter with one or more electrode assemblies) may be inserted into a patient's blood vessels such that the electrode assemblies are near the patient's nerves. The electrode assemblies may then be used for transvascular electrical stimulation of the patient's nerves. The disclosed devices may be optimized for rapid, temporary deployment in a patient and easy removal from the patient. The disclosed devices may be used, for example, for restoring breathing, treating conditions such as disuse muscle atrophy and chronic pain, or for any other procedures involving nerve stimulation. The disclosed devices may be used to treat acute or chronic conditions.

Medical Device Overview: Catheter and Electrode Assemblies

FIG. 1 illustrates a medical system 10 that includes a catheter 12 including a plurality of lumens and having two proximal electrode assemblies 14 and two distal electrode assemblies 16. The electrode assemblies 14 and 16 may be positioned on or within a tubular member or catheter body of catheter 12. Catheter 12 may be positioned within a patient through the patient's external or internal jugular veins 18, brachiocephalic veins 20, superior vena cava 22, brachial vein (not shown), radial vein (not shown), and/or left subclavian vein 24 such that the proximal electrode assemblies 14 are directed towards the left phrenic nerve 26, and the distal electrode assemblies 16 are directed laterally towards the right phrenic nerve 28. As such, when positioned, catheter 12 may receive signals from a control unit 30 and, using electrode assemblies 14 and 16, stimulate the left phrenic nerve 26 and/or the right phrenic nerve 28.

Figure 2:
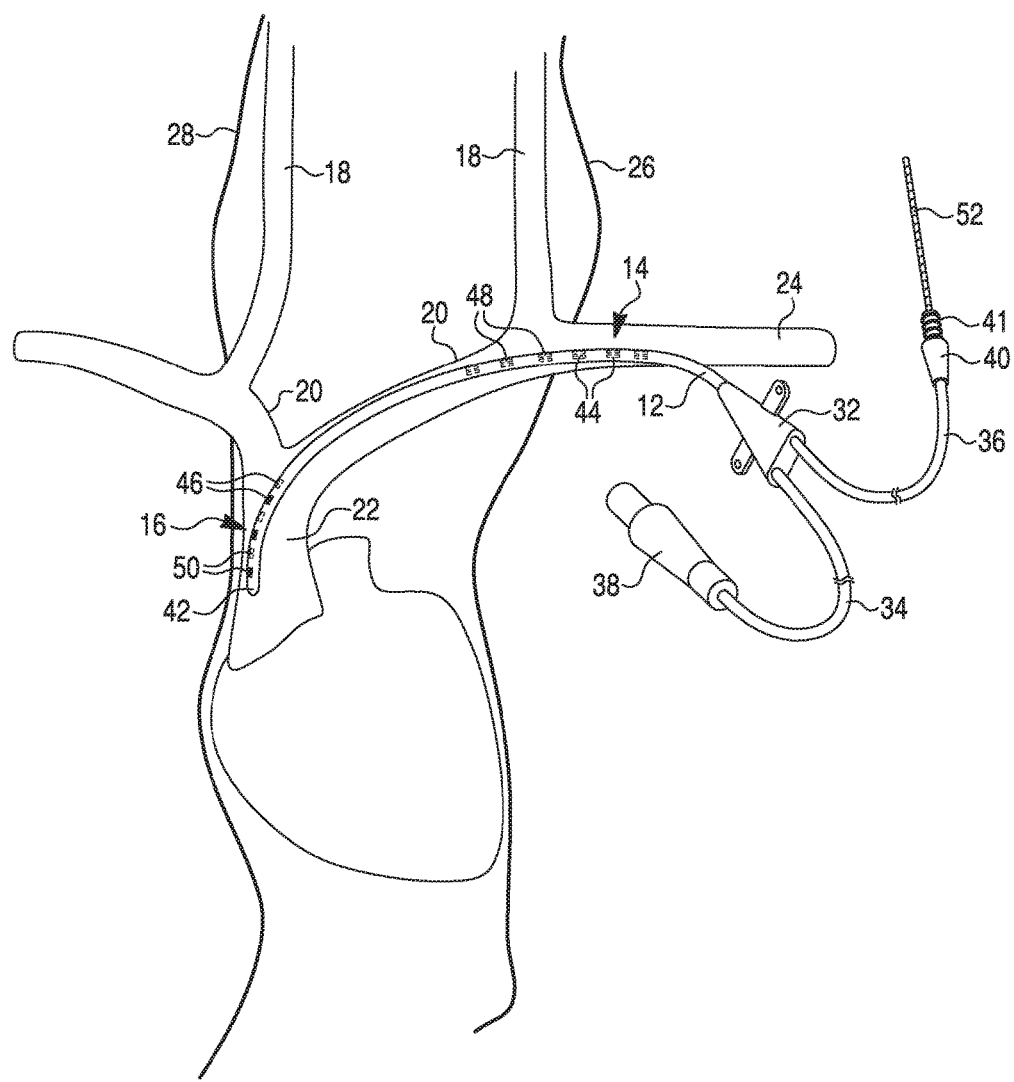
FIG. 2 illustrates a ventral view of an exemplary catheter having windows that align with nerve-stimulating electrodes within the catheter, inserted in a person's neck and upper torso, according to an exemplary embodiment.
Figure 3:
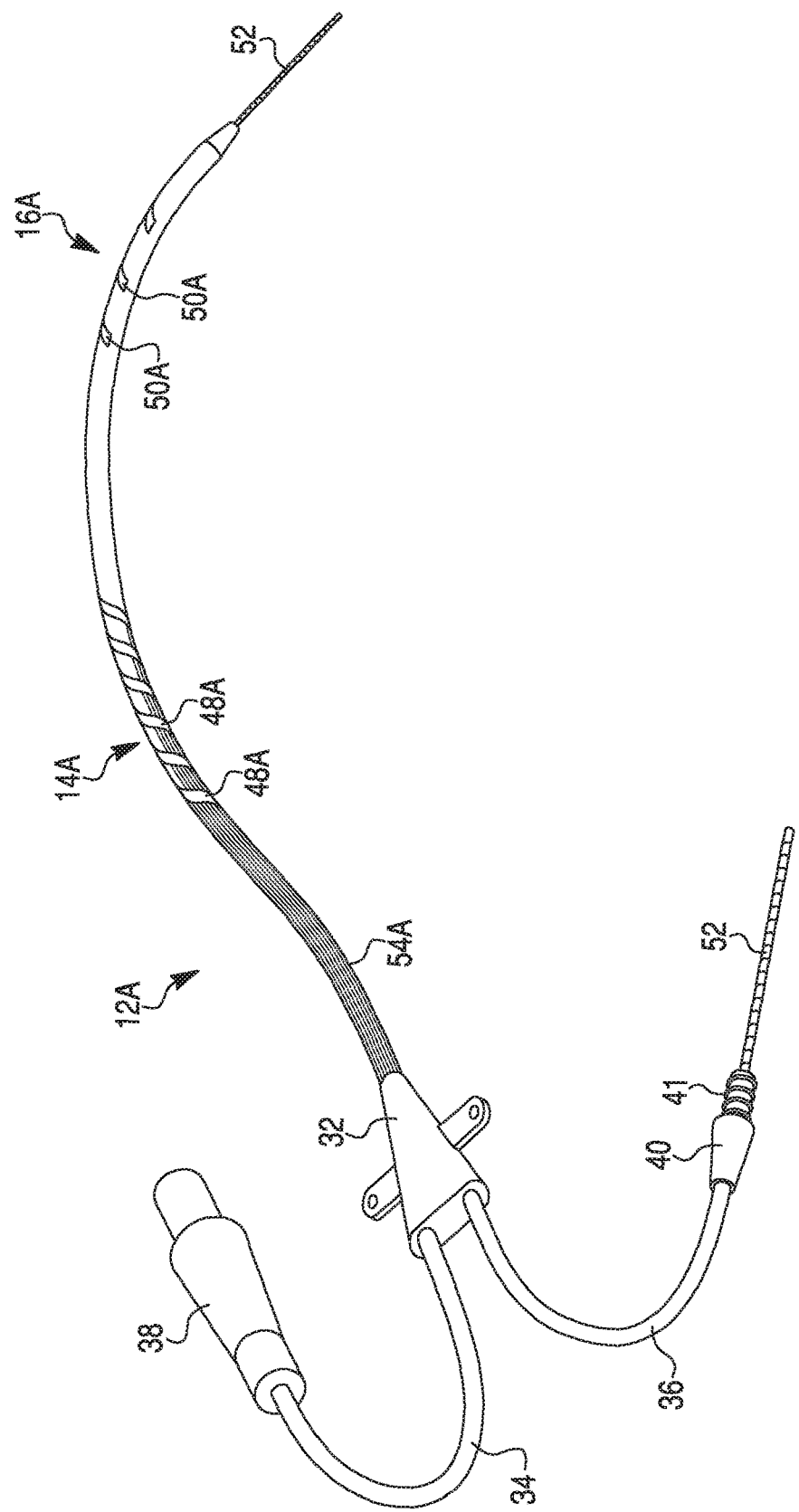
FIG. 3 illustrates a perspective view of a catheter with conductors and electrodes printed on the exterior of the catheter, according to an exemplary embodiment.

Catheter 12 may further include a manifold 32 that extends external to the patient. Electrical cable 34 and pigtail lumen 36 extend from manifold 32. Cable 34 and pigtail lumen 36 may include cable connectors 38 and 40 to connect external elements, and cable 34 may be coupled to electrical control unit 30 via cable connector 38. The cables 34 and 36 may be formed of electrical leads (not shown) that connect to electrode assemblies 14 and 16. Cable connectors 38 and 40 may be attached (e.g. by solder, crimp, PCB, etc.) to the cables 34 and 36, and one or both of cable connectors 38 and 40 may include a threading 41 (as shown in FIGS. 2 and 3). Alternatively or additionally, one or both of cable connectors 38 and 40 may include a push-to-pull compression fitting or a slip-lock fitting (not shown). Control unit 30 and other elements may be electronically connected to the components within catheter 12 to both send and receive signals and/or data to selectively stimulate electrode assemblies 14, 16 and/or monitor the patient and any response to the stimulation. Alternatively or additionally, cables 34 and 36 may include one or more lumens or fluid lines that connect to one or more internal lumens in catheter 12, and cable connectors 38 and 40 may form sealed connections with a fluid port or other source. Catheter 12 may also include an atraumatic distal tip 42.

As shown in FIG. 2, catheter 12 may include two axially extending rows of proximal apertures or windows 44. Each axially extending row includes proximal windows 44 positioned at the same circumferential position around the exterior of catheter 12, but at different axial positions along the exterior of catheter 12. The two rows of proximal windows 44 may be substantially aligned. For instance, as illustrated in FIG. 2, one proximal window 44 of a first row is located at the same axial position as a window of a second row, but at a different circumferential position around the exterior of the catheter 12. When positioned in a patient, the two rows of proximal windows 44 may be substantially posterior facing, and at least one proximal window 44 may face, abut or be positioned in the vicinity of the left phrenic nerve 26.

Catheter 12 may also include two axially extending rows of distal apertures or windows 46. Again, each axially extending row includes distal windows 46 positioned at the same circumferential position around the exterior of catheter 12, but at different axial positions along the exterior of catheter 12. The two rows of distal windows 46 may be unaligned such that one distal window 46 of a first row is axially between two distal windows 46 of a second row. For instance, as illustrated in FIG. 2, one distal window 46 of a first row is located at a different axial position and at a different circumferential position around the exterior of the catheter 12 than a window of the second row. When positioned in a patient, the two rows of distal windows 46 may be substantially laterally facing (to the patient's right), and at least one distal window 46 may face, abut, or be positioned in the vicinity of the right phrenic nerve 28. Therefore, in the example shown in FIG. 2, when viewed ventrally, the two unaligned rows of three distal windows 46 may appear as one row of six distal windows 46, because one row is anterior facing (shown as dark windows) and one row is posterior facing (shown as lighter windows).

The proximal windows 44 and the distal windows 46 may be positioned on catheter 12 such that one row of proximal windows 44 is circumferentially aligned (i.e., the same circumferential position but different axial position) with one row of distal windows 46, but another row of proximal windows 44 and another row of distal windows 46 are each circumferentially offset from the aligned rows on the catheter 12. Proximal electrode assemblies 14 may include individual proximal electrodes 48 that are positioned to be aligned with (e.g., radially inward of and underneath) proximal windows 44, and distal electrode assemblies 16 may include individual distal electrodes 50 that are positioned to be aligned with (e.g., radially inward of and underneath) distal windows 46. Windows 44, 46 may expose electrodes 48, 50, allowing for a conductive path between sets or pairs of electrodes 48, 50 and surrounding tissue, including the blood vessel lumen in which catheter 12 is inserted.

In one embodiment illustrated in FIG. 2, catheter 12 includes twelve proximal windows 44 (two rows of six windows 44) and six distal windows 46 (two rows of three windows 46). However, in other embodiments, the catheter 12 may include fewer or more rows and numbers of proximal or distal windows 46. For example, in other embodiments, the catheter 12 may include two, four, eight, ten, twelve, or more proximal windows 44 arranged in one, two, three, or more rows, and/or two, four, six, eight, ten, twelve or more distal windows 46 arranged in one, two, three, or more rows. The proximal windows 44 and distal windows 46 may be configured in pairs such that the catheter 12 has an even number of proximal windows 44 and an even number of distal windows 46. However, the number of windows 44 or 46 may also be an odd number.

The windows 44, 46 may be cut (e.g. by a laser, manual skive, drill, punch, etc.) through the exterior wall of catheter 12, or the windows 44, 46 may be formed by any other suitable method, such as during an extrusion process, 3-D printing, or other manufacturing process. The windows 44, 46 may extend along the longitudinal axis of catheter 12, or they may have a rectangular, oval, square, or any other shape. The windows 44, 46 may be apertures configured to allow electrical signals to travel from an interior lumen of the catheter 12 to the exterior of the catheter 12. In an additional or alternative embodiment, the windows 44, 46 may be covered by a material that allows electrical signals to pass through. As can be seen in the figures, the proximal windows 44 may be rotationally offset from the distal windows 46. In other words, in one embodiment, a straight line drawn proximally through a row of distal windows 46 does not necessarily pass through a row of proximal windows 44. In other embodiments, one or more rows of proximal windows 44 may be aligned with a corresponding row of distal windows 46. Furthermore, the characteristics of the proximal windows 44 may differ from the characteristics of the distal windows 46.

The dimensions of catheter 12 may be customized in accordance with the anatomy of a particular patient (e.g., different sizes of humans, pigs, chimpanzees, etc.). However, in some embodiments, the length of the section of the catheter 12 that includes the proximal windows 44 may be 10 cm or less, between 3-5 cm, or between 1-3 cm. The distance between two adjacent proximal windows 44 (whether the windows are circumferentially adjacent or longitudinally adjacent on the same row of windows) may be 5 cm or less, 3 cm or less, may be around 1 cm, or may be less than 1 cm. The length of the section of the catheter 12 that includes the distal windows 46 may be 6 cm or less, between 2-4 cm, or between 1-2 cm. The distance between two adjacent distal windows 46 (whether circumferentially adjacent or longitudinally adjacent on the same row of windows) may be 5 cm or less, 3 cm or less, may be around 1 cm, or may be less than 1 cm. The length of the section of the catheter 12 between proximal windows 44 and distal windows 46, which may be free of windows, may be 12 cm or less, 10 cm or less, or 8 cm or less. The windows 44, 46 may have a length of 6 mm or less, 5 mm or less, 4 mm or less, 3 mm or less, 2 mm or less, or 1 mm or less. In one embodiment, the windows 44, 46 may have a length that is less than the length of corresponding electrodes that are electrically exposed through the windows. These catheter dimensions are exemplary only, and the catheter 12 may have dimensions that vary from the above ranges and specific measurements. For neonatal applications, the distance between the distal electrodes and the proximal electrodes may be very small, perhaps less than 1 cm or even less than 1 mm. Alternatively, in this situation, a signal electrode array may contain electrode combinations which suitably serve to stimulate both the left phrenic nerve and the right phrenic nerve.

Additionally, catheter 12 may include windows 44, 46 in different configurations than discussed above. For example, catheter 12 may include more than two longitudinally extending rows of proximal windows 44 positioned at different circumferential positions. As such, catheter 12 may provide for more than two proximal electrode assemblies 14, or for two proximal electrode assemblies 14 to be positioned in different configurations in catheter 12. Alternatively or additionally, catheter 12 may be rotatable about the longitudinal axis such that windows 44, 46 at various circumferential positions may be positioned in different positions relative to the targeted nerves. Varying configurations may provide for various stimulation patterns with which catheter 12 may stimulate targeted nerves.

In one embodiment, medical system 10 may be assembled by positioning proximal and distal electrode assemblies 14, 16 within the outer, windowed tubular member of catheter 12 such that proximal electrodes 48 are at least partially exposed through proximal windows 44 and distal electrodes 50 are at least partially exposed through distal windows 46. The proximal electrode assemblies 14 may include the proximal electrodes 48 arranged and oriented to most effectively stimulate a nerve extending at transverse or right angles to the catheter 12 (e.g., the left phrenic nerve 26 in FIGS. 1 and 2), and the distal electrode assemblies 16 may include the distal electrodes 50 arranged and oriented to most effectively stimulate a nerve extending approximately parallel to the catheter 12 (e.g., the right phrenic nerve 28 in FIGS. 1 and 2). In an additional or alternative embodiment, the proximal electrode assemblies 14 may include proximal electrodes 48 arranged and oriented to most effectively stimulate a nerve extending approximately parallel to the catheter 12, and the distal electrode assemblies 16 may include distal electrodes 50 arranged and oriented to most effectively stimulate a nerve extending at transverse or right angles to the catheter 12. In the embodiments described above, the distal electrode assemblies 16 have been placed in a more distal location along catheter 12 than the proximal electrode assemblies 14. However, in other embodiments, the electrode assemblies 14, 16 may be rearranged within the catheter 12, and the proximal windows 44 and distal windows 46 of the catheter 12 may be configured to accommodate the alternative placement of the electrode assemblies 14, 16.

Distal tip 42 may be a tapered distal end portion of catheter 12. Distal tip 42 may be open at the distal end to allow a guide wire 52 to pass through and distally beyond catheter 12. Distal tip 42 may have a smaller circumference than the body of catheter 12. Distal tip 42 may be softer than other portions of catheter 12, be atraumatic, and have rounded edges. Distal tip 42 may be made of an aliphatic polyester-based thermoplastic polyurethane with a portion, for example, of 20% barium sulfate. Distal tip 42 may be formed and/or coupled to a remainder of catheter 12 by melting an extruded tube of thermoplastic polyurethane in a mold using, for example, an induction heater.

The medical system 10 may be used to rhythmically activate the diaphragm by inserting the catheter 12, with one or more electrode assemblies 14 and 16, percutaneously into central veins of a patient, as shown by FIG. 1. Guide wire 52 may be used to position catheter 12 within a patient. For example, the Seldinger technique may be used, in which guide wire 52 is inserted through a hypodermic needle into a vein. As in the example shown in FIGS. 1 and 2, the catheter 12 may be inserted into the left subclavian vein 24 and advanced into the superior vena cava 22. In an unillustrated example, catheter 12 may be inserted into the left jugular vein and advanced into the superior vena cava 22. In either example, catheter 12 may be inserted in a minimally-invasive way and may be temporarily placed into, and thus removable from, the patient. The distal tip 42 of the catheter 12 may then be passed over the guide wire 52 and advanced into the vein. The shape and mechanical properties of the catheter 12 may be designed to urge the catheter 12 to gently hug the vein wall in regions adjacent to the right and left phrenic nerves, as shown in FIG. 1. The guide wire 52 may also be positioned such that it is adjacent to the right and left phrenic nerves before the distal tip of the catheter 12 is passed over the guide wire 52. When the catheter 12 is positioned, the guide wire 52 may extend distal to the catheter 12 from distal tip 42, through an internal lumen in catheter 12, through pigtail lumen 36, and proximally out of a cable connector 40, as shown in FIG. 2.

Once the catheter 12 is fully inserted into the patient, various electrodes or electrode combinations can be tested to locate nerves of interest and to determine which electrodes most effectively stimulate the nerves of interest. For example, in one embodiment, testing may be done to locate the right phrenic nerve 28 and to determine which group of distal electrodes 50 in the distal electrode assemblies 16 most effectively stimulate the right phrenic nerve 28. Similarly, testing may be done to locate the left phrenic nerve 26 and to determine which group of proximal electrodes 48 in the proximal electrode assemblies 14 most effectively stimulate the left phrenic nerve 26. This testing and nerve location may be controlled and/or monitored via control unit 30, which may include testing programming and/or applications. For example, control unit 30 may test the electrodes and electrode combinations to determine which pair of bipolar distal electrodes 50 most effectively stimulate the right phrenic nerve 28, and which pair of bipolar proximal electrodes 48 most effectively stimulate the left phrenic nerve 26. Alternatively, control unit 30 may test the electrodes or electrode combinations to determine which tripolar or multipolar electrode combinations most effectively stimulate the phrenic nerves (for example, one cathode electrode and two anode electrodes, two cathode electrodes and one anode electrode, one cathode electrode and three anode electrodes, three cathode electrodes and one anode electrode, two cathode electrodes and two anode electrodes, one cathode electrode and four anode electrodes, four cathode electrodes and one anode electrode, one cathode electrode and five anode electrodes, five cathode electrodes and one anode electrode, etc.).

As a non-limiting example, testing could involve the use of a signal generator to systematically send electrical impulses to selected electrodes. By observing the patient's condition or by using sensors (either within or separate from the catheter 12), the ideal stimulation electrodes may be identified. Electrodes may serve as both stimulating electrodes and as sensing electrodes, and the medical system 10 may be integrated into a mechanical ventilator, which can be used to sense the patient's condition. Moreover, for example, control unit 30 may be programmed and/or activated to (a) select a first stimulation group of electrodes from the proximal electrode assemblies 14 to stimulate the left phrenic nerve 26, (b) select a second stimulation group of electrodes from the distal electrode assemblies 16 to stimulate the right phrenic nerve 28, (c) select a first stimulation current for the first stimulation group of electrodes to stimulate the left phrenic nerve 26, and (d) select a second stimulation current for the second stimulation group of electrodes to stimulate the right phrenic nerve 28. The selection of electrodes and current level may be pre-programmed or input based on the patient's characteristics, or the control unit 30 may test different electrode groups and current levels and monitor the patient's response to determine the electrode pairs and current levels. For example, the monitoring of the patient's response may include manual palpitation of the thoracic region, sensors to sense the movement of the patient's chest wall (e.g., accelerometers, optical devices, camera based sensors, etc.), airflow sensors, airway pressure sensors, central venous pressure sensors, etc. Control unit 30 may include a stimulation signal generator to generate the stimulation signals and to selectively transmit the generated signals to the selected electrodes.

Once ideal electrode combinations (e.g. pair, triplets, etc.) have been identified, an electrical potential may be created between a pair of selected bipolar electrodes, for example, a pair of proximal electrodes 48 each aligning with a proximal window 44. The arrangement of the electrodes 48 and the windows 44 may create an electrical field in the vicinity of windows 44, and thus in the vicinity of the targeted nerve, for example, the left phrenic nerve 26. During nerve stimulation, however, electrical current flows from one or more of the electrodes 48 to one or more of the other of the electrodes 48, flowing through the windows 44 and through the blood and surrounding tissues. The catheter 12 with windows 44 therefore acts as an insulating barrier that constrains and focuses the electrical field, rather than allowing the electrical field to expand radially outwards in all directions as the electrical field might with ring electrodes. The focused electrical field allows target nerve stimulation at lower, and thus safer, energy levels and avoids stimulating unwanted nerves or other structures. In some embodiments, the stimulation current may be between 10 and 6000 nC (nanocoulombs) or between 50-500 nC, reducing the risk of overstimulation or unwanted activation of nearby structures such as other nerves, muscles, or the heart.

In a further embodiment, any of the proximal electrodes 48 or the distal electrodes 50 may be used to measure electrical signals or other data from within the patient's body. In other words, in addition or alternatively to emitting or receiving electrical energy to produce a localized current for nerve stimulation, the electrodes 48, 50 may serve as sensors that receive electrical signals or other types of information from the patient.

Printed Ink Catheter

FIG. 3 illustrates an exemplary catheter 12A with electrode assemblies 14A, 16A and leads 54A printed directly onto the exterior of catheter 12A. Proximal electrode assemblies 14A, distal electrode assemblies 16A, and leads 54A may be formed by conductive inks (such as silver flakes or carbon flakes suspended in polymer or graphene ink). The conductive inks may be deposited and adhered directly onto the catheter 12A and sealed with an outer polyurethane or other flexible, insulating film or sheath, leaving the electrodes 48A, 50A of the electrode assemblies 14A, 16A at least partially exposed. The insulating film or sheath may be applied to the conductive inks that form electrode assemblies 14A, 16A and leads 54A, or may be applied to the catheter 12A as a whole. In some instances, the insulating film or sheath may be applied by 3-D printing or by other manufacturing processes. For example, at least one tubular sleeve (not shown) may be slid over at least a portion the exterior of catheter 12A. The tubular sleeve may be formed by extrusion, and/or the sleeve may be formed of a thin, thermoplastic material such as, but not limited to, polyamide, polyether block amide, polyurethane, silicone rubber, nylon, polyethylene, fluorinated hydrocarbon polymers, etc. Examples of polymer materials suitable for use in the sleeve are commercially available under the trademarks PEBAX™ and PELLETHANE™. The sleeve may be thermally bonded or mechanically attached to catheter 12A.

The exposed electrodes 48A, 50A may be coated with a conductive material (e.g., titanium nitride) in order to, for example, provide corrosion resistance and reduce the likelihood of silver oxide formation, which may be toxic. The conductive leads 54A electrically connect the proximal electrode assemblies 14A and the distal electrode assemblies 16A through cable 34 to control unit 30 or other electronics. The leads 54A connected to distal electrode assemblies 16A may travel proximally along catheter 12A beyond the proximal electrode assemblies 14A, for example, on the back side of catheter 12A in FIG. 3.

As shown in FIG. 3, proximal electrode assemblies 14A and distal electrode assemblies 16A may extend partially circumferentially around a portion of catheter 12A, and, for example, may be partially helical around a portion of the exterior of catheter 12A. Proximal electrode assemblies 14A and distal electrode assemblies 16A may be approximately 90 degrees displaced about a circumference of catheter 12A. For example, as shown in FIG. 3, proximal electrode assemblies 14A may extend helically 180 degrees around the front portion of the catheter 12A, and distal electrode assemblies 16A may extend helically 180 degrees around the top (plane of the paper) portion of the catheter 12A, and the proximal electrode assemblies 14A and distal electrode assemblies 16A are approximately 90 degrees displaced at right angles to the plane of the paper. As such, the partially helical electrodes 48A, 50A may increase the conductive surface area and broaden the electrical field produced by the electrodes 48A, 50A while still focusing the field on a portion of the circumference of the catheter 12A positioned proximate to, abutting, or facing the target nerve.

The use of printed electrodes and leads may reduce the overall complexity of the design while maximizing the useable catheter lumen space, without drastically changing the catheter profile or flexibility. The use of printed electrodes 14A, 16A and printed leads 54A also allows freedom of electrode position and electrode shape, permitting optimization of field focus and minimum energy for nerve recruitment and capture. Printed leads 54A may be helically disposed between printed electrodes 14A, 16A to allow for greater flexibility in bending the catheter 12A. Additionally, in some embodiments, the profile of the catheter 12A may be reduced because of the space saved by using electrodes printed on the exterior of the catheter 12A, for example, for use with neonate or other young patients. In an additional or alternative embodiment, one or several catheter lumens may be used for fluid delivery, blood sampling, central venous pressure monitoring, or to accommodate tools, sensors, or other objects. In another additional or alternative embodiment, several of the catheter lumens may be eliminated, allowing for larger catheter lumens and/or reducing the cross-sectional size of the catheter 12A.

Catheters Including Ribbon Cables

Figure 4:
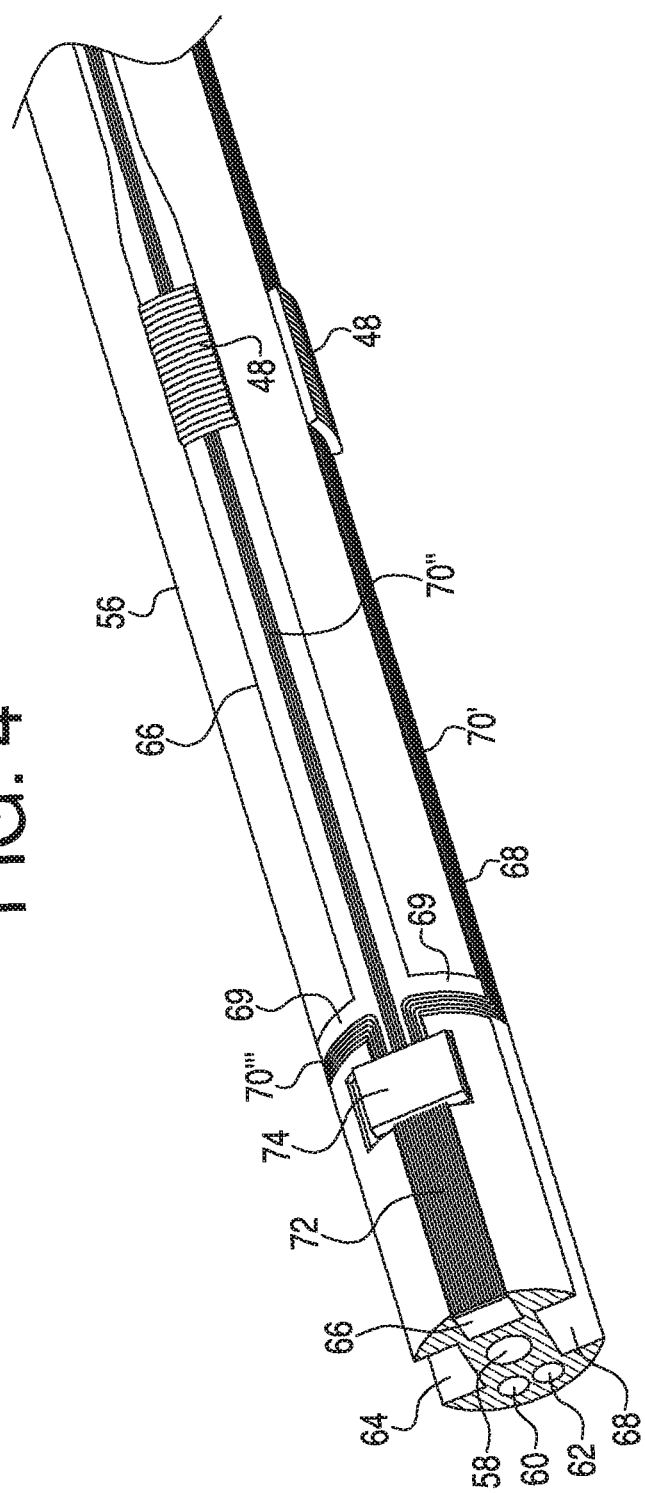
FIG. 4 illustrates a perspective view of a tubular member with conductors, an application specific integrated circuit, and electrodes, where the tubular member may be an internal part of a catheter, according to an exemplary embodiment.
Figure 5:
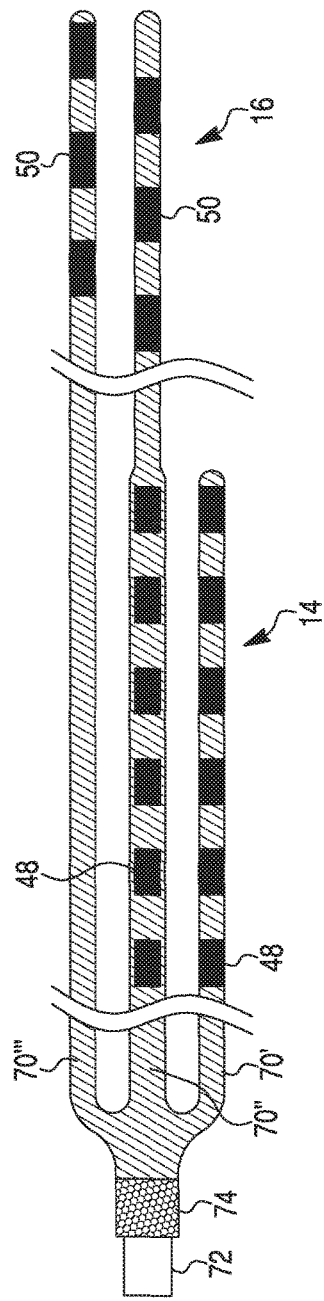
FIG. 5 illustrates a schematic view of the conductors, application specific integrated circuit, and electrodes of the exemplary embodiment shown in FIG. 4.
Figure 6:
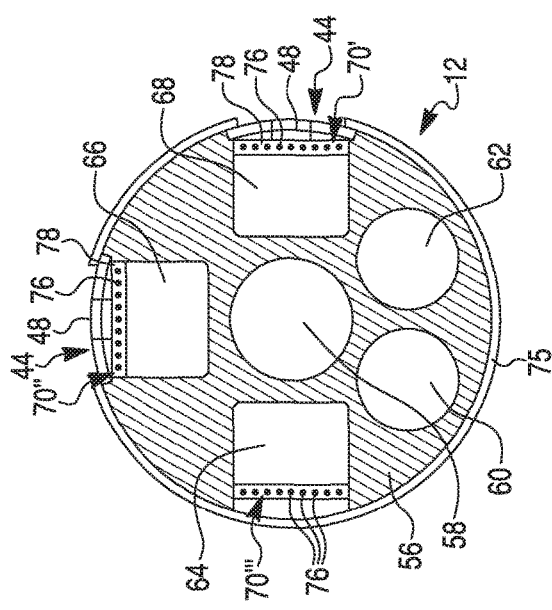
FIG. 6 illustrates a cross-sectional view of a catheter with an exemplary tubular member including conductors, electrodes, and lumens, according to an exemplary embodiment.

Referring now to FIGS. 4-6, a catheter body or tubular member 56 may form the interior of the catheter 12. As shown, tubular member 56 may include a guide wire lumen 58, at least two fluid lumens 60 and 62, and three lumens or grooves 64, 66, and 68. As discussed, guide wire 52 may be threaded though guide wire lumen 58. The fluid lumens 60 and 62 may be used to deliver and/or remove fluids at a treatment site. Additionally or alternatively, fluid lumens 60 and/or 62 may be used for other medical devices to treat, diagnose, or sense conditions at the surgical site. Grooves 64, 66, and 68 may, for example, be approximately rectangular in a cross-section. Grooves 64, 66, and 68 may extend radially to the outer surface of tubular member 56 and longitudinally along the tubular member 56. Grooves 64, 66, and 68 are exposed along at least a circumference and a portion of a length of tubular member 56 and may be spaced approximately 90 degrees from each other around the circumference of the tubular member 56. Grooves 64, 66, and 68 in tubular member 56 may accommodate electrical leads to connect control unit 30 to proximal electrodes 48 (shown in FIGS. 4 and 6) and distal electrodes 50. As shown, electrodes 48, 50 may extend longitudinally over a portion of tubular member 56 and may approximate the width of the grooves 64, 66, and 68 and/or the width of windows 44, 46.

In one aspect, the leads may be formed by ribbon cables 70', 70", and 70'''. As shown in FIG. 4, a connector feed 72 may be positioned within groove 66 and recessed within the outer perimeter of tubular member 56. Connector feed 72 may send and transmit signals to an application specific integrated circuit ("ASIC") 74. Connector feed 72 may also be formed by a ribbon cable. ASIC 74 may then be connected to three ribbon cables 70', 70", and 70''' that branch out and connect to the proximal electrode assemblies 14 and distal electrode assemblies 16. Ribbon cables 70', 70", and 70''' may be accommodated in grooves 64, 66, and 68 in tubular member 56. Partially circumferential grooves 69 extend around at least part of a circumference of the tubular member 56 to allow the ribbon cables 70', 70", and 70''' to branch out without extending away from or interfering with the tubular member 56 fitting within an outer covering of catheter 12.

Ribbon cables 70', 70", and 70''' are flexible and include multiple insulated leads 76 (some of which are labeled in FIG. 6) connected along their lengths to form a single, flexible planar structure. The planar structure is flexible to allow the formation of other shapes, such as bends and/or corrugations. The leads 76 within ribbon cables 70', 70", and 70''' may include a wire or a rod-like conductive member. Leads 76 are surrounded by a layer of non-conducting material 78, such as insulation (FIG. 6). Ribbon cables 70', 70", and 70''' may be similar to printed circuits formed using thin flexible polyimide substrates with copper plated conductors. Typical dimensions include an insulation base layer about 0.0381 mm (0.0015 in) thick, a copper conductor about 0.0381 mm (0.0015 in) thick by 0.0508 mm (0.002 in) wide, an insulation cover layer about 0.0381 mm (0.0015 in) thick, and a lateral spacing between conductors of about 0.0381 mm (0.0015 in). The ribbon cables 70', 70", and 70''' may be secured within the grooves 64, 66, and 68 by application of a heat shrink polyolefin tube around the outside of tubular member 56. Windows may be formed by ablating the heat shrink tube locally over the electrodes 48, 50 using a $CO_2$ laser. As such, any of the leads 76 may be uninsulated at a point along the length of catheter 12 and coupled to an electrode 48, 50, such as, for example, a flexible foil electrode or an electrode formed according to any of the embodiments described herein and exposed through a window 44, 46 of catheter 12.

In one example, connector feed 72 may include approximately 8 electrical leads in a ribbon cable, and ribbon cables 70', 70", and 70''' may include enough electrical leads 76 to send electrical signals to each electrode 48, 50 of the proximal electrode assemblies 14 and distal electrode assemblies 16. For instance, connector feed 72 may include an electrical lead for each of power, ground, data stream, anode signal, cathode signal, and leads to send and receive signals from various elements in catheter 12. Ribbon cables 70 connect to each electrode 48, 50 of the electrode assemblies 14, 16 in order to stimulate the targeted nerves.

ASIC 74 may serve to direct the signals received from connector feed 72. For example, based on the received signals, ASIC 74 may direct electrical signals to one or a plurality of the electrodes 48, 50 of the proximal electrode assemblies 14 and the distal electrode assemblies 16. As such, there may be only one connection and/or connector at the proximal end of catheter 12 to transmit electrical or other signals distally from, for example, control unit 30, to the proximal and distal electrode assemblies 14 and 16, providing further space within tubular member 56 for the fluid lumens 60 and 62, additional medical instruments, and/or allowing the tubular member 56 and the remainder of the catheter 12 to be smaller. ASIC 74 allows for a reduction in conductors in the connector feed 72, and thus reduces the number of couplings between connector feed 72 and ASIC 74, improving reliability and reducing cost. Moreover, ASIC 74 permits the use of a connector with 8 or 9 pins, rather than a connector with 19 pins, further improving reliability and reducing the risk of signal interference or misalignment.

FIG. 5 illustrates a schematic view of the connector feed 72, ASIC 74, ribbons cables 70', 70", 70''', and the electrode assemblies 14, 16. Ribbon cables 70', 70", 70''' may be three separate ribbon cables, or may be one ribbon cable that branches out into three ribbon cables. As discussed, connector feed 72 may include 8 conductor leads 54 connected to ASIC 74. ASIC 74 connects to ribbon cables 70', 70", 70''' to selectively deliver signals to one or a plurality of the proximal electrodes 48 or the distal electrodes 50. Proximal electrodes 48 and distal electrodes 50 may be mounted or otherwise physically and electrically connected to the corresponding ribbon cable 70', 70", 70'''. In one example, ribbon cables 70', 70", 70''' may include one lead 76 per electrode 48, 50, with the particular lead 76 terminating in an uninsulated portion where the lead 76 is coupled to the electrode 48, 50 by mechanical rivet, solder, crimping, or another technique.

As shown in FIGS. 4 and 5, one ribbon cable 70' may include one proximal electrode assembly 14 with six proximal electrodes 48. One ribbon cable 70" may include one proximal electrode assembly 14 with six proximal electrodes 48 and one distal electrode assembly 16 with three distal electrodes 50. One ribbon cable 70''' may include one distal electrode assembly 16 with three distal electrodes 50. ASIC 74 may decode the signals from connector feed 72 and determine if a particular electrode 48, 50 is to be an anode or a cathode, so each of the ribbon cables 70', 70", 70''' may only require one lead for each of the electrodes 48, 50 connected to that ribbon cable 70', 70", 70'''. In this situation, ribbon cable 70' may include six leads 76 to connect to the six proximal electrodes 48. Ribbon cable 70" may include nine leads 76 to connect to the six proximal electrodes 48 and three distal electrodes 50. Ribbon cable 70''' may include as few as three leads 76. The proximal electrodes 48 of the two proximal electrode assemblies 14 may be aligned (positioned at the same axial position and different circumferential positions), and the distal electrodes 50 of the two distal electrode assemblies 16 may be displaced (positioned at different axial positions and different circumferential positions). The electrodes 48, 50 may also take different orientations and arrangements in order to locate and/or stimulate the target nerves.

FIG. 6 illustrates an axial cross-sectional view of a proximal portion of the catheter 12, including tubular member 56 and an outer layer or sheath 75, at a position of proximal electrode assemblies 14. As shown, guide wire lumen 58, fluid lumens 60 and 62, and grooves 64, 66, and 68 longitudinally pass through tubular member 56. Ribbon cables 70', 70", and 70''' with leads 76 are positioned within grooves 64, 66, and 68. Proximal electrodes 48 are mounted over ribbon cables 70' and 70" and are exposed through proximal windows 44. Although not shown, distal electrodes 50 are mounted and/or connected to ribbon cables 70" and 70''' and exposed through distal windows 46 in a similar manner to the proximal electrodes 48.

In another aspect of this disclosure, the tubular member 56 may include printed ink conductors and electrodes similar to that shown in FIG. 3. In this example, the printed ink conductors may extend distally from ASIC 74 and branch out in a similar manner as discussed above, but with the printed ink conductors extending along the circumferential surface of the tubular member 56. The printed ink conductors may connect to printed electrodes, and signals may be selectively transmitted via the ASIC 74 to the electrodes through the printed ink conductors.

Tubular member 56 may be extruded polyurethane (or any other suitable biocompatible material). Sheath 75 fitting over tubular member 56 may be made of any biocompatible plastic or other material. In one aspect, sheath 75 is a 0.002 m thick polyolefin shrink tube that may be positioned around tubular member 56 and shrunk down using a heat gun or other heating source. Windows 44 may be formed by ablating the heat shrink tube locally over the electrodes 48, 50 using a $CO_2$ laser. Alternatively, sheath 75 may be a 3-D printed insulation layer with windows 44 over electrodes 48, 50 formed by open portions during the 3-D printing.

FIG. 7A illustrates a longitudinal cross-sectional view of a portion of one groove 66 in the tubular member 56, and FIG. 7B illustrates an exploded view of a portion of a ribbon cable 70" that may fit within groove 66. The configuration in FIG. 7A shows an arrangement where electrode 48 is coupled at one end of the electrode to the appropriate lead 76 of ribbon cable 70" and corrugations 82 in ribbon cable 70" pass beneath electrode 48. Such an arrangement may be used if the distance between electrodes 48, 50 is short, and using as many corrugations as possible provides maximum longitudinal and rotational flexibility for the ribbon cables 70', 70", and 70''' in the catheter. Alternatively or additionally, as in FIG. 7B, corrugations 82 in ribbon cables 70', 70", and 70''' may be located between electrodes only, and not under the electrodes As shown in FIG. 7A, ribbon cable 70" may be coupled to proximal electrode 48 via a connection 80. Connection 80 electrically and physically connects electrode 48 to the appropriate lead 76 of ribbon cable 70" that corresponds to electrode 48. Connection 80 may be, for example, a wire connection with solder or a rivet. Electrode 48 may longitudinally overlap with ribbon cable 70", and may extend longitudinally and be positioned radially underneath a portion of tubular member 56. A portion of electrode 48 may be exposed through window 44 and may be partially covered by a non-insulating and/or conductive cover 49.

Proximal electrode 48 may be exposed via proximal window 44 in sheath 75. A proximal electrode 48, along with the other electrodes 48, 50, may be a sheet Platinum-Iridium (Ptlr) electrode with a thickness of approximately 0.0381-0.0508 mm (0.0015-0.002 in). Ribbon cable 70" may be coupled to the other proximal electrodes 48 and the distal electrodes 50 in the same manner as illustrated in FIG. 7A. Electrodes 48, 50 may be various other known electrode assemblies, for example, ring electrodes fixed to the exterior of catheter 12. Electrodes 48, 50 may also be formed of other conductive materials, including platinum, gold, stainless steel, titanium nitride, MP35N, palladium, or another appropriate material. Electrodes 48, 50 may also be coupled to ribbon cables 70', 70", and 70''' with conductive adhesive, heat fusion, crimping, riveting, microwelding, or another appropriate method. Electrodes 48, 50 may also include an insulating coating over a portion of the electrodes 48, 50 that may facilitate directional targeting of one or more nerves.

Each ribbon cable 70', 70", and 70''' may also include corrugations 82 within at least one or more portions of grooves 64, 66, and 68. Corrugations 82 may provide greater longitudinal and lateral flexibility and bendability of the catheter 12 and the internal components. Corrugations 82 may pass underneath an electrode 48, as shown in FIG. 7A. Alternatively or additionally, corrugations 82 may be positioned along ribbon cables 70', 70", and 70''' between longitudinally adjacent electrodes 48, 50, as shown in FIG. 7B. In this aspect, a filler block 84 may support electrode 48, 50 and ribbon cable 70". A filler strip 86 may include contours 88 that mirror the corrugations 82. Contours 88 may extend radially inwardly to fit within corrugations 82. Filler strip 86 may be positioned on a radially outward side of ribbon cable 70" to support the corrugations 82 of ribbon cable 70" between electrodes 48, 50. Corrugations 82 of ribbon cable 70" may be unsupported or open on the radially inward side of corrugations opposite to filler strip 86 and contours 88, which may increase the longitudinal or lateral flexibility. Filler blocks 84 and filler strips 86 may be elastomeric and may be sized to fit within grooves 64, 66, and 68 of tubular member 56.

Figure 8:
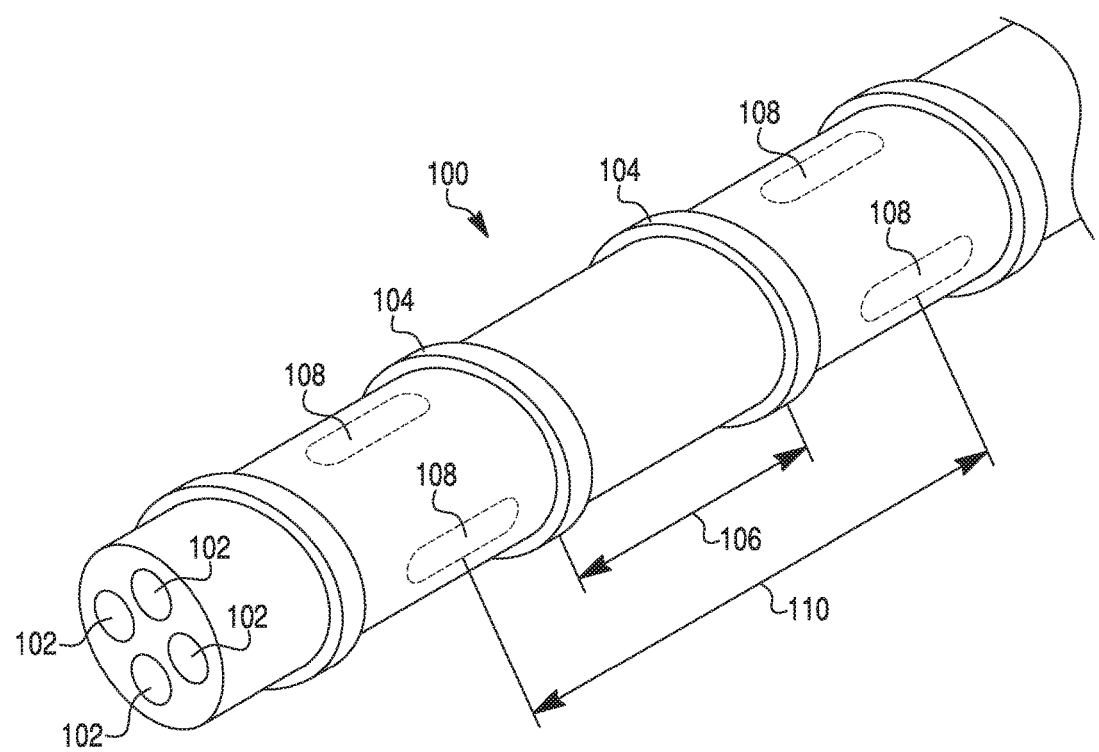
FIG. 8 illustrates a perspective view of a portion of a tubular member with axial lumens and a radial extension, according to an exemplary embodiment.

FIGS. 8-10 illustrate an alternative embodiment of the disclosure, including tubular member 100 and helical ribbon cable 101 that may be radially surrounded by an outer layer, sleeve, or sheath 175 to form a catheter 112 to stimulate target nerves as discussed above, according to another aspect of this disclosure.

FIG. 8 illustrates a portion of tubular member 100. Tubular member 100 is sized to fit within sheath 175 in a similar manner to tubular member 56 (FIG. 10). Tubular member 100 includes a series of lumens 102, which may include a guide wire lumen and fluid lumens that may function as discussed above. Tubular member 100 includes a radial extension 104. Radial extension 104 extends radially outward from tubular member 100. Radial extension 104 may be integrally formed of the same material as tubular member 100, or may be a separate element attached to or positioned around tubular member 100. Radial extension 104 may helically extend along an outer surface of tubular member 100 and include a helical pitch 106. Electrode locations 108 may be located such that there are at least portions of radial extension 104 between electrode locations 108, as shown in FIG. 8, to form an electrode pitch 110. One or both of tubular member 100 and radial extension 104 may be formed by, for example, extrusion, molding, or 3-D printing using XYZ and rotary motions to deposit a flexible polymer around a mandrel, with some or all of the polymer being sacrificial.

FIG. 9 illustrates a portion of helical ribbon cable 101 with electrodes 114 mounted on helical ribbon cable 101. FIG. 9 shows a top view of cable 101 in a straight, flat configuration prior to its placement around tubular member 100. Helical ribbon cable 101 may be formed and may function similarly to ribbon cables 70', 70", and 70''' with leads 76 surrounded by non-conducting material 78 as discussed above. Additionally, electrodes 114 may be coupled to ribbon cable 101 as with electrodes 48, 50 and ribbon cables 70', 70", and 70'''. Helical ribbon cable 101 may include an upper conductor 103 having multiple leads that communicate with the upper electrodes 114, and a lower conductor 105 also having multiple leads communicating with the lower electrodes 114. Conductors 103 and 105 are surrounded by and separated by insulating layers 107.

Electrodes 114 are mounted on helical ribbon cable 101 at an angle to the axis of the helical ribbon cable 101 such that the electrodes lie at the correct axially disposed angle when the helical ribbon cable 101 is wrapped around the tubular member 100 in the helical recess defined by radial extensions 104. After wrapping the helical ribbon cable 101 around the tubular member, the electrodes 114 adopt the alignment shown by locations 108 in FIG. 8. In one example, if the electrodes 114 are to be oriented with the electrodes' shorter dimension disposed circumferentially around the tubular member 100 after helical ribbon cable 101 is helically wrapped, then electrodes 114 may be mounted on helical ribbon cable 101 at approximately a 59 degree angle relative to a longitudinal axis of the helical ribbon cable 101. The length of helical ribbon cable 101 between paired electrodes 114 corresponds to an electrode pitch 110 between paired electrode locations 108. Therefore, when the helical ribbon cable 101 is wrapped around tubular member 100 between radial extensions 104, paired electrodes 114 align with electrode locations 108. For example, if the electrode pitch 110 is about 10 mm, and the tubular member 100 has an outside diameter of about 3.2 mm, then the distance between sets of paired electrodes on helical ribbon cable 101 is approximately 23 mm.

As shown in FIG. 10, catheter 112 may include tubular member 100 and helical ribbon cable 101 positioned within sheath 175. Electrodes 114 and helical ribbon cable 101 may function as discussed above, without interfering with lumens 102 and other radially internal elements of tubular member 100. Moreover, electrodes 114 may be electrically and physically coupled to helical ribbon cable 101 via connection 116. Connection 116 may be, for example, a wire connection, a solder connection, a rivet, or another mechanical and electrical connection to mechanically and electrically connect electrode 114 to helical ribbon cable 101. Electrodes 114 may then be exposed via an electrode window 118. Sheath 175 may also radially surround tubular member 100, and sheath 175 may comprise one or more insulating layers of flexible polyimide, shrink tubing, and/or a flexible filler.

FIG. 11 illustrates an aspect of the present disclosure that may be incorporated in any of the foregoing aspects. As shown in FIG. 11, each electrode 114 may be coupled to a small ASIC 120. For example, helical ribbon cable 101 may be coupled to a tubular member 100A as part of a catheter 112A. Tubular member 100A may include guide wire lumen 58, two fluid lumens 60 and 62, and grooves 64, 66, and 68, similar to as shown in FIG. 4. Small ASICs 120 may be positioned within grooves 64, 66, and 68 radially between electrodes 48, 50 and guidewire lumen 58. The small ASICs 120 allow for a reduction of conductive leads 76. For example, unless an ASIC 120 is located locally for each electrode 48, 50, there must be a separate lead 76 for each electrode 48, 50. With an ASIC 120 specific to each electrode, the ASIC 120 may decode a signal from a control unit and determine whether the signal applies to that particular electrode 48, 50. Therefore, helical ribbon cable 101, or other ribbon cable in other aspects of this disclosure, would be connected through the electrode-specific ASICs 120 to all electrodes 48, 50, and the helical ribbon cable 101 would only need five conductive leads 76 (an anode reference, a cathode reference, a power, a ground, and a data line) for any number of electrodes 48, 50. It is further noted that locally located ASICs 120 require a groove or recess in the tubular member 100A, but may also be incorporated in other tubular members or catheters of this disclosure. For instance, grooves or recesses may be extruded in tubular member 100A, and tubular member 100A may be extruded, 3-D printed, or otherwise formed to include helical lumens such that the grooves or recesses do not interfere with the lumens. Grooves or recesses may also be helical, and the helical grooves or recesses, along with helical lumens, may be formed by extruding the tubular member as with longitudinal grooves, and lumens, and then heat setting the tubular member in a twisted state. Each electrode 114 may be exposed through a window (similar to as shown in FIG. 10), or may be partially covered by a non-insulating and/or conductive element 121, as shown in FIG. 11.

Once positioned within a patient, the catheter 112A of FIG. 11, with helical ribbon 101 and small ASICs 120, may be used to stimulate the target nerves as discussed above. In particular, the conductive leads of the helical ribbon cable 101 may be reduced because each lead of the same helical ribbon cable 101 may connect to each small ASIC 120. Based on the signals through the leads of the helical ribbon cable 101, each small ASIC 120 controls whether the electrical signals through leads are emitted through the particular electrodes 114. Similar to the example shown in FIGS. 4-6, the catheter 112A of FIG. 11 may only include one connection at the proximal end of catheter 112A to transmit electrical or other signals distally to the proximal and distal electrode assemblies 14 and 16, providing further space within tubular member 100A for the fluid lumens 60 and 62, additional medical instruments, and/or allowing the tubular member 100A and catheter 112A to be smaller.

Wireless Connections to Control Unit

Figure 12:
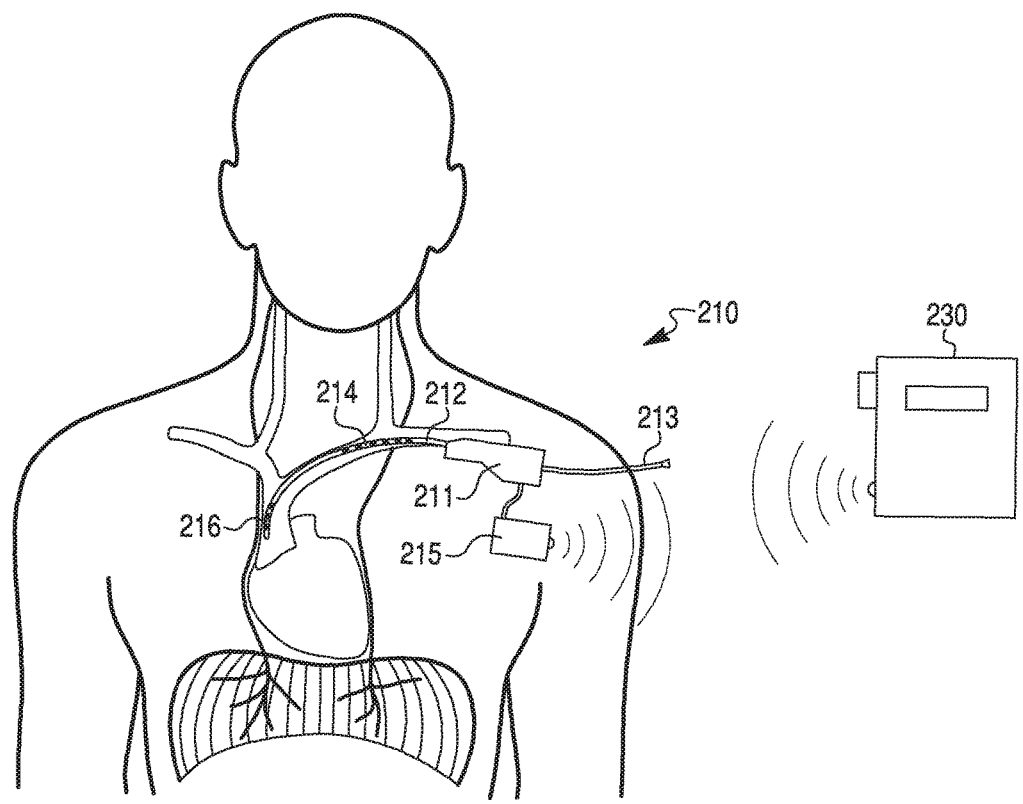
FIG. 12 illustrates the anatomy of selected nerves and blood vessels in a person's neck and upper torso along with an exemplary catheter and control unit connected via a wireless connection, according to an exemplary embodiment.

FIG. 12 illustrates an alternative medical system 210 with similar elements to the medical system 10 of FIG. 1 shown by 200 added to the reference numbers. Medical system 210 includes a wireless connection from control unit 230 to catheter 212. Catheter 212 may be inserted and positioned as discussed with respect to FIG. 1. Catheter 212 may include proximal and distal electrode assemblies 214, 216 that are exposed through proximal and distal windows as discussed above.

Instead of proximal connector 32, catheter 212 may include a manifold or hub 211 at a proximal end or coupled to the proximal end of catheter 212. Hub 211 may be positioned external to the patient when catheter 212 is inserted. Hub 211 may include a plurality of lumens that may connect to the guide wire and fluid lumens within catheter 212. In one aspect, hub 211 may be connected to a fluid port 213 and a wireless unit 215. Fluid port 213 may include one lumen connected through hub 211 to a lumen in catheter 212, or fluid port 213 may include a plurality of lumens connected through hub 211 to lumens within catheter 212, including a guide wire port. Wireless unit 215 may include a battery and a receiver/transmitter. The receiver/transmitter of wireless unit 215 may be in wireless communication with control unit 230, via, for example, a Bluetooth connection. As such, control unit 230 may send signals to and receive signals from wireless unit 215. Wireless unit 215 may then be coupled to one or more leads or ribbon cables to transmit electrical signals distally to the proximal and distal electrode assemblies 214, 216, and the signals may be distributed via one or more ASICs within catheter 212 to stimulate a target nerve.

Wireless unit 215, or catheter 212 itself, may also include a wireless information unit (not shown), for example, an RFID tag or wireless chip, or other unique coded information related to the catheter 212 including, for example, the catheter serial number and construction change level. For instance, as improvements to the catheter are made over time, each improvement is recorded as a change level. This change level may, for example, include an electrode material change or an electrode surface finish. These changes may permit the use of a more effective stimulation pulse stream. The control unit 230 may evaluate the change level code and determine whether a new stimulation program installed on the control unit 230 is applicable to that catheter 210, as the software of control unit 230 may also be updated periodically. The change level code may avoid the creation of "generic" pirated clones by detecting false codes and preventing the system from operating if a false code is detected. As such, this would also reduce the risks to the patient, medical professional, and manufacturer by eliminating the risk of inferior devices being improperly used without the proper clinical testing and approval. The wireless information unit may further record usage data for catheter 212, including, for example, time of day of use, duration of use, number of times used, and other information related to communications from control unit 230. Hub 211 with wireless unit 215 does not require a wired connection between the control unit 230 and the catheter 212, reducing the assembly time for a medical professional and reducing the risk of signal interference, misalignment, cable snagging, and other human errors.

Alternatively, though not shown, wireless unit 215 may receive all data wirelessly from control unit 230, but the low voltage power necessary for the receiver in wireless unit 215 may be delivered by a low-cost three conductor cable from the control unit 230. This arrangement allows the system to operate for long periods of time without the risk of running low on battery power. Although this arrangement requires a cable for power, the arrangement nevertheless results in a minimal number of pins in the connections to the control unit, thereby enhancing reliability and reducing the risk of misalignment.

Radiopaque Catheters and Orientation Indicators

Figure 13:
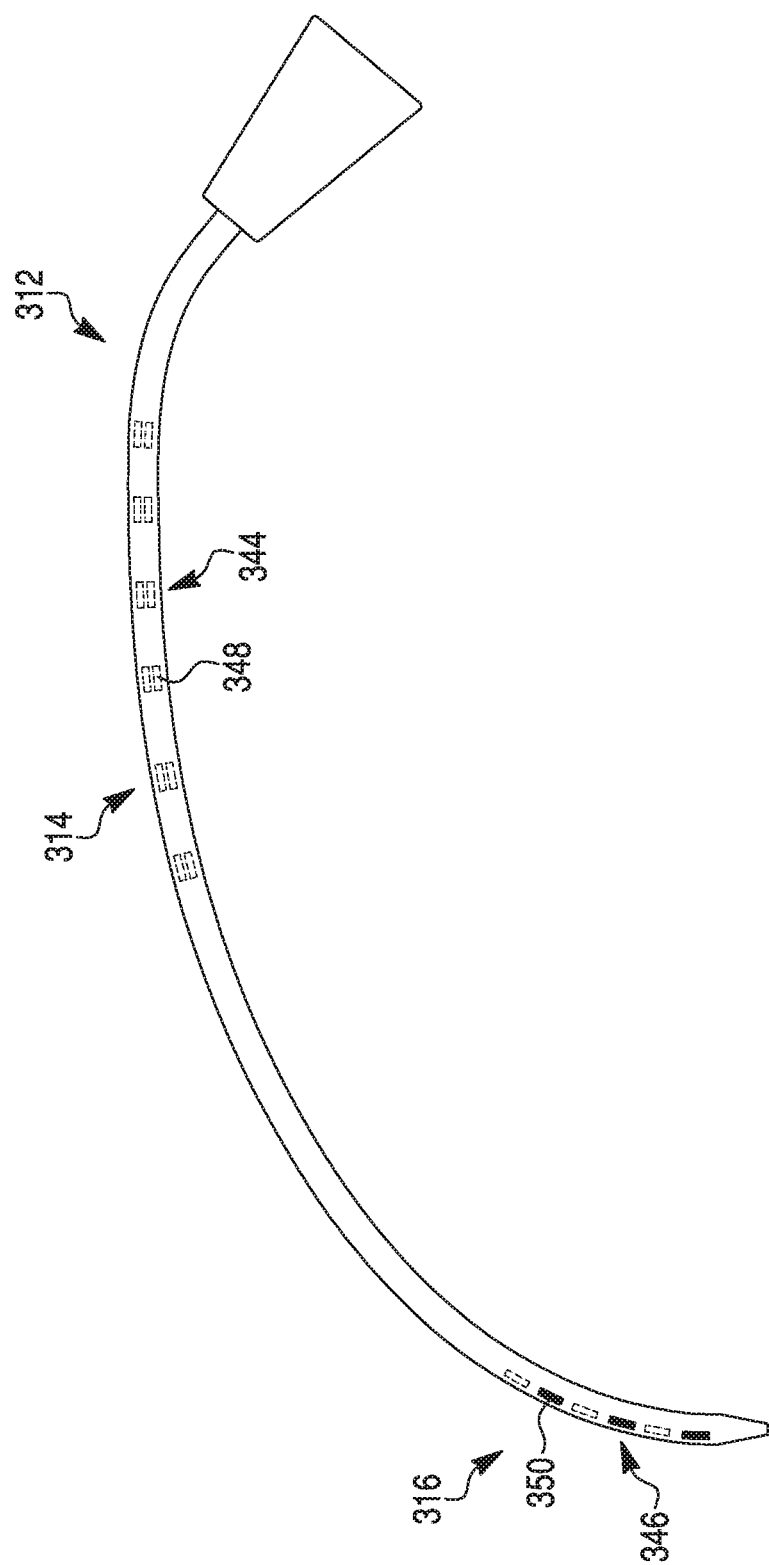
FIG. 13 illustrates an exemplary catheter with radiopaque electrodes, according to an exemplary embodiment.
Figure 14:
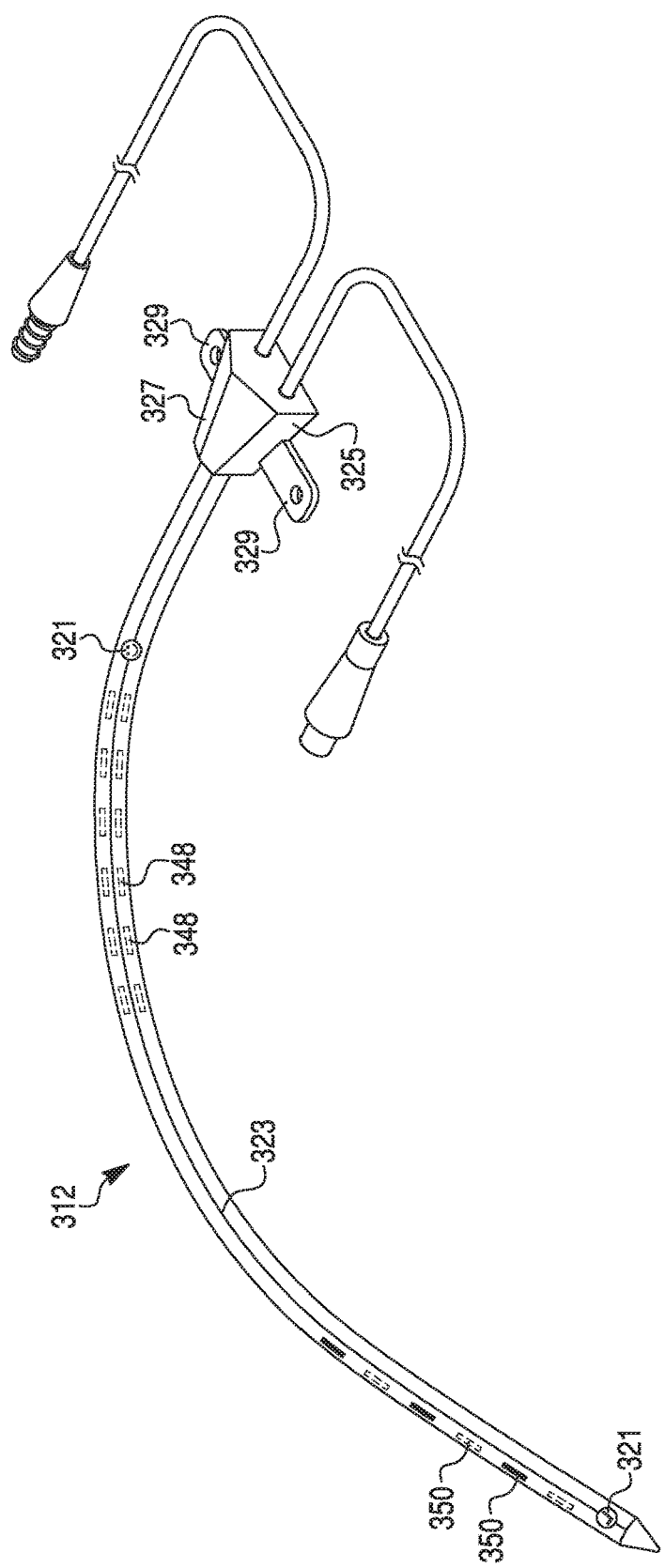
FIG. 14 illustrates an exemplary catheter with radiopaque electrodes and orientation-aiding indicators, according to an exemplary embodiment.

FIGS. 13 and 14 illustrate an alternative catheter 312 with similar elements to the catheter 12 of FIG. 1 shown by 300 added to the reference numbers. Aspects shown in FIGS. 13 and 14 may be incorporated in any of the foregoing catheter examples in order to ensure that the catheter 312 is aligned properly. As shown in FIG. 13, catheter 312 may be radiopaque and may be viewed via one or more imaging systems, for example, via fluoroscopy, X-ray, or other imaging methods. Catheter 312 may be made to be radiopaque by using a polymer that is approximately 20% $BaSO_4$, or by printing radiopaque ink on the exterior of the catheter. Radiopaque catheter 312 may include two proximal electrode assemblies 314, each with six proximal electrodes 348 exposed via proximal windows 344, and two distal electrode assemblies 316, each with three distal electrodes 350 exposed via distal windows 346. Electrodes 348, 350 may also be radiopaque, for example, containing 10% Platinum-Iridium (PtIr), and may appear to be darker than the radiopaque catheter 312.

FIG. 13 shows an anterior view of radiopaque catheter 312 properly aligned such that proximal electrodes 348 face substantially posteriorly (to the patient's back) to stimulate the left phrenic nerve 26, and distal electrodes 350 face substantially laterally (to the patient's right) to stimulate the right phrenic nerve 28. When viewed anteriorly, the proximal electrodes 348 may appear in two aligned rows of six electrodes in the center of the catheter 312. The distal electrodes 350 may appear in a single row of six electrodes positioned toward the lateral (patient's right) edge of the catheter 312. Moreover, the proximal electrodes 348 and three alternating distal electrodes 350 may appear to be darker than the catheter shaft 312, even though these electrodes are posterior facing. Three alternating distal electrodes 350 may appear to be even darker than the other electrodes as these electrodes are anterior facing. If the catheter 312 and electrodes 348, 350 appear differently than shown and described, the catheter 312 and electrodes 348, 350 are likely improperly positioned. As such, a medical professional may use this visualization to ensure that the catheter 312 and electrodes 348, 350 are positioned properly when stimulating or preparing to stimulate target nerves.

FIG. 14 illustrates an additional example of catheter 312 that is radiopaque and may aid in ensuring the catheter 312 and electrodes 348, 350 are properly positioned. As with FIG. 13, when viewed anteriorly via an imaging system, a properly positioned catheter 312 may include two rows of six proximal electrodes 348 in the center of the catheter 312, and one row of six distal electrodes 350 toward the lateral (patient's right) edge of the catheter 312. The proximal electrodes 348 and three alternating distal electrodes 350 may appear darker than the catheter 312, and three alternating distal electrodes 350 may appear even darker than the other electrodes.

As shown in FIG. 14, catheter 312 may further include one or more radiopaque markers 321. For example, catheter 312 may include a one radiopaque marker 321 at a distal end of the catheter 312, and one radiopaque marker 321 at a proximal end of the catheter 312. Radiopaque markers 321 may be formed by printing or otherwise applying radiopaque ink to the catheter 312. When viewed with an imaging system, the orientation and/or appearance of the radiopaque markers 321 may allow a medical professional to determine whether the catheter 312 is properly positioned and/or oriented. For example, the distal radiopaque marker 321 may be a check mark, and the proximal radiopaque marker 321 may be a smiley face, as shown in FIG. 14. When viewed anteriorly, if the checkmark is longer on the right side, and the smiley face is right-side up, then the catheter 312 is properly oriented. Otherwise, orientation is not proper, and the user may adjust the position of catheter 312.

Catheter 312 may include a further radiopaque orientation marker, for example, orientation stripe 323. Orientation stripe 323 may extend longitudinally along at least a portion of the length of the catheter 312 such that when viewed anteriorly with an imaging system, the orientation stripe 323 passes through the middle of the catheter 312. Orientation stripe 323 may bisect or align with a midpoint of the radiopaque markers 321. Orientation stripe 323 may be positioned on catheter 312 such that, when the catheter 312 and electrodes 348, 350 are properly positioned and viewed anteriorly using an imaging system, orientation stripe 323 passes evenly between the two rows of proximal electrodes 348 and passes to the medial (patient's left) side of the one row of distal electrodes 350. Orientation stripe 323 may be formed during the formation of the catheter 312, for example, during an extrusion. Orientation stripe 323 may include a different color or pattern, may be laser marked, may be printed with radiopaque ink, may be a radiopaque wire introduced into a dedicated lumen of the catheter body, or may be formed by any other appropriate methods. If the catheter 312 is not properly positioned, the catheter 312 may be adjusted until the electrodes 348, 350, radiopaque markers 321, and orientation stripe 323 appear when viewed anteriorly as illustrated in FIG. 14.

Orientation stripe 323 may be also be used to control the orientation of the catheter 312 while inserting catheter 312 into a patient without taking an x-ray or using another visualization technique. For example, orientation stripe 323 may run longitudinally from the distal end to the proximal end of catheter 312. Therefore, as long as the catheter 312 is not undergoing torsion, a medical professional is able to determine the orientation of the distal end, which is inserted into the patient and thus not visible without imaging technology, by observing the location of the orientation stripe 323 on the proximal end that extends proximally from the patient.

Radiopaque catheter 312 may also include an orientation hub 325. For example, the shape and size of orientation hub 325 may be such that orientation hub may be sutured or otherwise attached in only one orientation. Orientation hub 325 may have an apex 327 that circumferentially aligns with orientation stripe 323 on catheter 312, and which is opposite to a flat bottom that may rest on a patient's chest or another surface. The flat bottom may also include two attachment members or suture tabs 329 extending from the bottom such that the bottom may be coupled to other elements in the proper orientation. Additionally or alternatively, orientation hub 325 may include a wireless unit as discussed above with respect to FIG. 12.

Catheter 312 may include all or a portion of the aforementioned positioning markers. Additionally, a medical professional may use different positioning markers to ensure the catheter 312 is positioned properly as different markers may exhibit greater visibility depending on the patient, the imaging system, and other variables. Catheter 312 and the various positioning and orientation markers may be modified and/or customized depending on the patient. For example, fewer electrodes 348, 350 may be used with a smaller patient, for example, a neonate. Alternatively, a patient with abnormal nerve locations may require a different catheter orientation and/or arrangement.

Other Alternative Embodiments and Interpretation of Terms

As noted earlier, any of the components and features of any of the embodiments disclosed herein may be combined and used in any suitable combinations with any of the other components and features disclosed herein. However, for the sake of example, some ways in which the described example embodiments may be varied include:

different numbers of electrodes;
different electrode configurations;
different electrode fixing (crimp, adhesive, microweld, rivet, etc.);
different electrode shape (round, oval, circular, rectangular, etc.);
different electrode material;
different electrode surface areas;
different electrode spacing;
different number or shapes of lumens;
different window shape/dimensions;
different catheter profile (e.g., +/−9 Fr);
different catheter length; and/or
different steering mechanism.

As mentioned above, the use of the various catheter embodiments allows for an increase in the number of available lumens within the catheter. The size of the catheter may also be reduced, for example, for use in neonatal patients or patients who require a smaller catheter. Ribbon cables increase the longitudinal flexibility of the catheter and the electrode connections during the manipulation and use of the catheter. Using ASICs and/or wireless connections reduces the number of cables and connections the medical professional must properly connect and avoid during various procedures, while still properly and accurately stimulating various internal nerves. Additionally, radiopaque catheters, radiopaque electrodes, radiopaque markers, and orientation markers may aid a medical professional in locating the position of the catheter and orienting the catheter in order to most effectively stimulate the patient's nerves.

Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to";

"connected," "coupled," or any variant thereof, means any connection or coupling, either direct or indirect, between two or more elements; the coupling or connection between the elements can be physical, electrical, or a combination thereof;

"herein," "above," "below," and words of similar import, when used to describe this specification, shall refer to this specification as a whole, and not to any particular portions of this specification;

"or," in reference to a list of two or more items, covers all of the following interpretations of the word: any of the items in the list, all of the items in the list, and any combination of the items in the list; and the singular forms "a," "an," and "the" also include the meaning of any appropriate plural forms.

Words that indicate directions such as "vertical," "transverse," "horizontal," "upward," "downward," "forward," "backward," "inward," "outward," "left," "right," "front," "back," "top," "bottom," "below," "above," "under," and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

We claim:

1. A catheter, comprising:
an outer sheath defining a plurality of apertures therethrough;
a body defining at least one longitudinal lumen therein, wherein at least a portion of the body is radially inward of the outer sheath, and the apertures are radially outward of the lumen;
a plurality of electrodes positioned in or on the catheter, each electrode being electrically exposed through an aperture of the plurality of apertures; and
a ribbon cable extending through the lumen and including a plurality of leads, the plurality of leads being electrically connected to the plurality of electrodes,
wherein the plurality of apertures includes a plurality of proximal apertures and a plurality of distal apertures, the plurality of proximal apertures including two longitudinally extending rows of proximal apertures, and wherein the outer sheath includes (1) a first radiopaque feature at a distal portion of the sheath for confirming an orientation of the distal apertures and (2) a second radiopaque feature at a proximal portion of the sheath and positioned circumferentially opposite to a line extending between the two rows of proximal apertures.

2. The catheter of claim 1, wherein the lumen is a groove exposed along the circumference of the body along at least a portion of the length of the body, the groove being at least partially covered by the outer sheath.

3. The catheter of claim 1, wherein the plurality of leads are at least partially surrounded by a non-conducting material; and wherein the ribbon cable is electrically connected to at least one electrode via a connection.

4. The catheter of claim 1, wherein the ribbon cable includes a plurality of corrugations.

5. The catheter of claim 4, further including at least one filler positioned within at least a portion of the corrugations, and wherein the corrugations are positioned radially inward of at least one electrode.

6. The catheter of claim 1, further including: at least one fluid lumen and a guide wire lumen, and a connector feed and an application specific integrated circuit radially inward or outward of the outer sheath, wherein the application specific integrated circuit connects the connector feed to the ribbon cable.

7. The catheter of claim 6, wherein the ribbon cable includes three branches of ribbon cable;
wherein the at least one longitudinal lumen includes three longitudinal lumens spaced circumferentially around an exterior of the body and radially inward of the outer sheath; and
wherein the three branches extend distally from the application specific integrated circuit, and each of the three branches connects to at least one electrode through a corresponding longitudinal lumen.

8. The catheter of claim 7, wherein one branch of the three branches includes at least one lead that electrically connects at least one proximal electrode and at least one other lead that electrically connects at least one distal electrode.

9. The catheter of claim 1,
wherein the plurality of distal apertures includes two longitudinally extending rows comprising a first row of distal apertures and a second row of distal apertures; and
wherein one row of the two rows of proximal apertures is circumferentially aligned with the first row of distal apertures.

10. The catheter of claim 9, wherein the first radiopaque feature is for confirming an orientation of the first row of distal apertures relative to the second row of distal apertures.

11. The catheter of claim 9, wherein the other of the two rows of proximal apertures is circumferentially offset from both the first row of distal apertures and the second row of distal apertures.

12. The catheter of claim 10, further including a hub, wherein the hub includes an orientation feature and a port, wherein the port is configured to couple the hub to a proximal portion of the catheter in a particular orientation.

13. The catheter of claim 1, wherein the lumen and the ribbon cable are recessed from an outer surface of the body.

14. The catheter of claim 1, wherein the lumen is a first lumen, and the ribbon cable is a first ribbon cable, and wherein the catheter further comprises a second ribbon cable extending through a second lumen defined by the body.

15. The catheter of claim 14, wherein the first lumen and the second lumen are spaced circumferentially around an exterior of the body.

16. The catheter of claim 1, wherein the ribbon cable includes three or more leads arranged in a row.

17. The catheter of claim 1, wherein the ribbon cable has a single, flexible planar structure.

18. The catheter of claim 1, wherein the outer sheath has an inner surface exposed to the at least one longitudinal lumen and an outer surface comprising the outermost surface of at least a portion of the catheter.

19. A catheter, comprising:
an outer sheath defining a plurality of apertures therethrough;
a body defining at least one lumen recessed within an outer surface of the body, wherein the apertures are radially outward of the lumen, and wherein an inner surface of the sheath is exposed to the ribbon cable, and an outer surface of the sheath is the outermost surface of at least a portion of the catheter;
a plurality of electrodes positioned in or on the catheter, each electrode being electrically exposed through an aperture of the plurality of apertures; and
a ribbon cable extending through the lumen, in a single flexible planar configuration, and including at least three leads arranged in a row, the plurality of at least three leads being electrically connected to the plurality of electrodes.

20. The catheter of claim 19, wherein the lumen is a first lumen, and the ribbon cable is a first ribbon cable, and wherein the catheter further comprises a second ribbon cable extending through a second lumen defined by the body.

21. The catheter of claim 19, wherein the lumen is a groove exposed along the circumference of the body along at least a portion of the length of the body, the groove being at least partially covered by the outer sheath.

22. The catheter of claim 19, wherein the plurality of apertures includes a first row of proximal apertures, a second row of proximal apertures, a first row of distal apertures, and a second row of distal apertures, and wherein the first row of proximal apertures is circumferentially aligned with one of either the first row of distal apertures or the second row of distal apertures, and the second row of proximal apertures is circumferentially offset from both the first row of distal apertures and the second row of distal apertures.

* * * * *

UNITED STATES PATENT AND TRADEMARK OFFICE
CERTIFICATE OF CORRECTION

PATENT NO. : 10,293,164 B2
APPLICATION NO. : 15/606867
DATED : May 21, 2019
INVENTOR(S) : John E. Nash et al.

Page 1 of 1

It is certified that error appears in the above-identified patent and that said Letters Patent is hereby corrected as shown below:

In the Claims

Claim 19, at Column 24, Lines 31–32, delete "the plurality of at least three leads" and insert --the at least three leads--

Signed and Sealed this
Sixth Day of August, 2019

Andrei Iancu
*Director of the United States Patent and Trademark Office*